(12) United States Patent
Moskowitz et al.

(10) Patent No.: US 10,537,442 B2
(45) Date of Patent: *Jan. 21, 2020

(54) BIDIRECTIONAL FIXATING INTERVERTEBRAL IMPLANT SYSTEM

(71) Applicant: Moskowitz Family LLC, Rockville, MD (US)

(72) Inventors: Ahmnon D. Moskowitz, Rockville, MD (US); Pablo A. Valdivia Y. Alvarado, Cambridge, MA (US); Mosheh T. Moskowitz, Rockville, MD (US); Nathan C. Moskowitz, Rockville, MD (US)

(73) Assignee: Moskowitz Family LLC, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,117

(22) Filed: Apr. 3, 2018

(65) Prior Publication Data

US 2018/0221173 A1 Aug. 9, 2018

Related U.S. Application Data

(63) Continuation of application No. 15/894,471, filed on Feb. 12, 2018, now Pat. No. 10,390,969, which is a
(Continued)

(51) Int. Cl.
*A61B 17/064* (2006.01)
*A61B 17/70* (2006.01)
(Continued)

(52) U.S. Cl.
CPC ........ *A61F 2/4611* (2013.01); *A61B 17/0642* (2013.01); *A61B 17/7064* (2013.01);
(Continued)

(58) Field of Classification Search
CPC ........ A61F 2/4611; A61F 2/4465; A61F 2/447; A61F 2002/2835; A61F 2002/30133;
(Continued)

(56) References Cited

U.S. PATENT DOCUMENTS 2,360,942 A 10/1944 Ellerstein et al.
4,064,881 A 12/1977 Meredith
(Continued)

FOREIGN PATENT DOCUMENTS

FR 2727003 5/1996
WO 2004093749 11/2004
WO 2006091503 8/2006

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Pedro Philogene
(74) *Attorney, Agent, or Firm* — Fish & Richardson P.C.

(57) ABSTRACT

A self-drilling bone fusion screw apparatus is disclosed which includes at least first and second sliding boxes. A first screw member having a tapered end and a threaded body is disposed within the first sliding box, and a second screw member having a tapered end and a threaded body disposed within the second sliding box. An adjuster adjusts the height of the sliding boxes. The screw members are screwed into vertebral bodies in order to fuse the vertebral bodies together. A plurality of the self-drilling bone fusion screw apparatuses may be attached together and/or integrated via a plate or cage. Also disclosed is a cervical facet staple that includes a curved staple base and at least two prongs attached to the bottom surface of the curved staple base.

20 Claims, 38 Drawing Sheets

Related U.S. Application Data continuation of application No. 13/210,157, filed on Aug. 15, 2011, now Pat. No. 9,889,022, which is a continuation of application No. 13/084,543, filed on Apr. 11, 2011, now Pat. No. 8,353,913, and a continuation of application No. 13/108,982, filed on May 16, 2011, now Pat. No. 9,005,293, said application No. 13/084,543 is a continuation of application No. 11/842,855, filed on Aug. 21, 2007, now Pat. No. 7,942,903, said application No. 13/108,982 is a continuation of application No. 11/842,855, filed on Aug. 21, 2007, now Pat. No. 7,942,903, which is a continuation-in-part of application No. 11/536,815, filed on Sep. 29, 2006, now Pat. No. 7,846,188, which is a continuation-in-part of application No. 11/208,644, filed on Aug. 23, 2005, now Pat. No. 7,704,279.

(60) Provisional application No. 60/670,231, filed on Apr. 12, 2005.

(51) Int. Cl.
| | | |
|---|---|---|
| *A61B 17/80* | (2006.01) | |
| *A61B 17/86* | (2006.01) | |
| *A61B 17/88* | (2006.01) | |
| *A61B 17/92* | (2006.01) | |
| *A61F 2/44* | (2006.01) | |
| *A61F 2/46* | (2006.01) | |
| *A61F 2/28* | (2006.01) | |
| *A61F 2/30* | (2006.01) | |
| *A61B 17/00* | (2006.01) | |
| *A61B 17/17* | (2006.01) | |

(52) U.S. Cl.
CPC ........ *A61B 17/809* (2013.01); *A61B 17/8635* (2013.01); *A61B 17/8875* (2013.01); *A61B 17/8894* (2013.01); *A61B 17/92* (2013.01); *A61F 2/447* (2013.01); *A61F 2/4465* (2013.01); *A61B 17/0644* (2013.01); *A61B 17/1757* (2013.01); *A61B 17/86* (2013.01); *A61B 2017/00407* (2013.01); *A61B 2017/0641* (2013.01); *A61B 2017/0648* (2013.01); *A61B 2017/922* (2013.01); *A61F 2002/2835* (2013.01); *A61F 2002/3055* (2013.01); *A61F 2002/30133* (2013.01); *A61F 2002/30387* (2013.01); *A61F 2002/30448* (2013.01); *A61F 2002/30507* (2013.01); *A61F 2002/30579* (2013.01); *A61F 2002/30604* (2013.01); *A61F 2002/30772* (2013.01); *A61F 2002/30878* (2013.01); *A61F 2002/30879* (2013.01); *A61F 2002/30904* (2013.01); *A61F 2002/448* (2013.01); *A61F 2002/4475* (2013.01); *A61F 2002/4627* (2013.01); *A61F 2002/4681* (2013.01); *A61F 2002/4687* (2013.01); *A61F 2220/005* (2013.01); *A61F 2220/0025* (2013.01); *A61F 2230/0015* (2013.01); *A61F 2250/0007* (2013.01)

(58) Field of Classification Search
CPC .. A61F 2002/30387; A61F 2002/30448; A61F 2002/30507; A61F 2002/3055; A61F 2002/30579; A61F 2002/30604; A61F 2002/30772; A61F 2002/30878; A61F 2002/30879; A61F 2002/30904; A61F 2002/4475; A61F 2002/448; A61F 2002/4627; A61F 2002/4681; A61F 2002/4587; A61F 2220/0025; A61F 2220/005; A61F 2230/0015; A61F 2250/0007; A61B 17/0642; A61B 17/7064; A61B 17/809; A61B 17/8635; A61B 17/8875; A61B 17/8894; A61B 17/92; A61B 17/0644; A61B 17/1757; A61B 17/86; A71B 2017/00407; A71B 2017/0641; A71B 2017/0648; A71B 2017/922
USPC ................ 623/17.11–17.16; 606/246–279
See application file for complete search history.

(56) References Cited

U.S. PATENT DOCUMENTS

| | | |
|---|---|---|
| 4,554,914 A | 11/1985 | Kapp et al. |
| 4,599,086 A | 7/1986 | Doty |
| 4,636,217 A | 1/1987 | Ogilvie et al. |
| 4,904,261 A | 2/1990 | Dove et al. |
| 4,960,420 A | 10/1990 | Goble et al. |
| 4,997,432 A | 3/1991 | Keller |
| 5,005,749 A | 4/1991 | Aranyi |
| 5,062,850 A | 11/1991 | MacMillan et al. |
| 5,123,926 A | 6/1992 | Pisharodi |
| 5,290,312 A | 3/1994 | Kojimoto et al. |
| 5,405,391 A | 4/1995 | Henderson et al. |
| 5,413,583 A | 5/1995 | Wohlers |
| 5,454,819 A | 10/1995 | Knoepfter |
| 5,514,180 A | 5/1996 | Heggeness et al. |
| 5,609,635 A | 3/1997 | Michelson |
| 5,660,188 A | 8/1997 | Groiso |
| 5,665,122 A | 9/1997 | Kambin |
| 5,667,472 A | 9/1997 | Finn et al. |
| 5,713,912 A | 2/1998 | Porter |
| 5,782,832 A | 7/1998 | Larsen et al. |
| 5,865,848 A | 2/1999 | Baker |
| 5,888,223 A | 3/1999 | Bray, Jr. |
| 5,916,224 A | 6/1999 | Esplin |
| 5,951,574 A | 9/1999 | Stefanchik et al. |
| 5,960,522 A | 10/1999 | Boe |
| 5,968,054 A | 10/1999 | Yeatts et al. |
| 5,976,136 A | 11/1999 | Bailey et al. |
| 6,126,689 A | 10/2000 | Brett |
| 6,224,602 B1 | 5/2001 | Hayes |
| 6,235,034 B1 | 5/2001 | Bray |
| 6,322,562 B1 | 11/2001 | Wolter |
| 6,342,074 B1 | 1/2002 | Simpson |
| 6,368,350 B1 | 4/2002 | Erickson et al. |
| 6,375,682 B1 | 4/2002 | Fleischmann et al. |
| 6,419,704 B1 | 7/2002 | Ferree |
| 6,432,106 B1 | 8/2002 | Fraser |
| 6,454,807 B1 | 9/2002 | Jackson |
| 6,458,159 B1 | 10/2002 | Thalgott |
| 6,527,804 B1 | 3/2003 | Gauchet et al. |
| 6,533,818 B1 | 3/2003 | Weber et al. |
| 6,558,423 B1 | 5/2003 | Michelson |
| 6,562,074 B2 | 5/2003 | Gerbec et al. |
| 6,572,653 B1 | 6/2003 | Simonson |
| 6,579,318 B2 | 6/2003 | Varga et al. |
| 6,582,468 B1 | 6/2003 | Gauchet |
| 6,613,055 B2 | 9/2003 | Di Emidio |
| 6,629,998 B1 | 10/2003 | Lin |
| 6,641,614 B1 | 11/2003 | Wagner et al. |
| 6,652,533 B2 | 11/2003 | O'Neil |
| 6,655,243 B2 | 12/2003 | Anderson et al. |
| 6,706,070 B1 | 3/2004 | Wagner et al. |
| 6,716,247 B2 | 4/2004 | Michelson |
| 6,719,794 B2 | 4/2004 | Gerber |
| 6,723,126 B1 | 4/2004 | Berry |
| 6,733,532 B1 | 5/2004 | Gauchet et al. |
| 6,733,535 B2 | 5/2004 | Michelson |
| 6,764,491 B2 | 7/2004 | Frey et al. |
| 6,770,094 B2 | 8/2004 | Fehling et al. |
| 6,824,564 B2 | 11/2004 | Crozet |
| 6,852,117 B2 | 2/2005 | Orlowski |
| 6,890,355 B2 | 5/2005 | Michelson |
| 6,904,308 B2 | 6/2005 | Frisch et al. |
| 6,953,477 B2 | 10/2005 | Berry |

(56) References Cited

U.S. PATENT DOCUMENTS

| | | |
|---|---|---|
| 6,955,671 B2 | 10/2005 | Uchikubo |
| 6,962,606 B2 | 11/2005 | Dove et al. |
| 6,972,019 B2 | 12/2005 | Michelson |
| 6,974,480 B2 | 12/2005 | Messerli et al. |
| 7,030,904 B2 | 4/2006 | Adair et al. |
| 7,033,394 B2 | 4/2006 | Michelson |
| 7,037,258 B2 | 5/2006 | Chatenever et al. |
| 7,077,864 B2 | 7/2006 | Byrd et al. |
| 7,097,615 B2 | 8/2006 | Banik et al. |
| 7,135,043 B2 | 11/2006 | Nakahara et al. |
| 7,211,112 B2 | 5/2007 | Baynham et al. |
| 7,232,464 B2 | 6/2007 | Mathieu et al. |
| 7,238,203 B2 | 7/2007 | Bagga et al. |
| 7,326,248 B2 | 2/2008 | Michelson |
| 7,442,209 B2 | 10/2008 | Michelson |
| 7,442,299 B2 | 10/2008 | Lee et al. |
| 7,588,573 B2 | 9/2009 | Berry |
| 7,615,059 B2 | 11/2009 | Watschke et al. |
| 7,618,456 B2 | 11/2009 | Mathieu et al. |
| 7,628,816 B2 | 12/2009 | Mageri et al. |
| 7,704,279 B2 | 4/2010 | Moskowitz et al. |
| 7,727,246 B2 | 6/2010 | Sixto et al. |
| 7,758,617 B2 | 7/2010 | Lott et al. |
| 7,776,047 B2 | 8/2010 | Fanger et al. |
| 7,776,093 B2 | 8/2010 | Wolek |
| 7,803,162 B2 | 9/2010 | Marnay et al. |
| 7,846,207 B2 | 12/2010 | Lechmann et al. |
| 7,862,616 B2 | 1/2011 | Lechmann et al. |
| 7,875,076 B2 | 1/2011 | Mathieu et al. |
| 7,887,591 B2 | 2/2011 | Aebi et al. |
| 7,942,903 B2 | 5/2011 | Moskowitz et al. |
| 7,959,675 B2 | 6/2011 | Gately |
| 7,972,363 B2 | 7/2011 | Moskowitz et al. |
| 7,985,255 B2 | 7/2011 | Bray et al. |
| 8,029,512 B2 | 10/2011 | Paltzer |
| 8,034,060 B2 | 10/2011 | Keren et al. |
| 8,105,367 B2 | 1/2012 | Austin et al. |
| 8,114,162 B1 | 2/2012 | Bradley |
| 8,137,405 B2 | 3/2012 | Kostuik et al. |
| 8,167,949 B2 | 5/2012 | Tyber |
| 8,268,000 B2 | 9/2012 | Waugh et al. |
| 8,273,127 B2 | 9/2012 | Jones et al. |
| 8,328,851 B2 | 12/2012 | Curran |
| 8,328,872 B2 | 12/2012 | Duffield et al. |
| 8,353,913 B2 | 1/2013 | Moskowitz et al. |
| 8,403,986 B2 | 3/2013 | Michelson |
| 8,414,651 B2 | 4/2013 | Tyber et al. |
| 8,419,797 B2 | 4/2013 | Biedermann et al. |
| 8,425,607 B2 | 4/2013 | Waugh et al. |
| 8,540,774 B2 | 9/2013 | Kueenzi et al. |
| 8,613,761 B2 | 12/2013 | Lindermann et al. |
| 8,728,165 B2 | 5/2014 | Parry et al. |
| 8,790,405 B2 | 7/2014 | Biedermann et al. |
| 8,845,731 B2 | 9/2014 | Weiman |
| 8,882,813 B2 | 11/2014 | Jones et al. |
| 9,333,095 B2 | 5/2016 | Beaurain et al. |
| 9,393,130 B2 | 7/2016 | Suddaby |
| 9,895,238 B2* | 2/2018 | Moskowitz ........ A61B 17/0642 |
| 9,907,674 B2* | 3/2018 | Moskowitz ........ A61B 17/0642 |
| 10,238,505 B2* | 3/2019 | Moskowitz ............. A61F 2/447 |
| 2002/0068977 A1 | 6/2002 | Jackson |
| 2002/0143338 A1 | 10/2002 | Orbay et al. |
| 2003/0130737 A1 | 7/2003 | McGahan et al. |
| 2004/0015315 A1 | 1/2004 | Kreider |
| 2004/0088054 A1 | 5/2004 | Berry |
| 2004/0177531 A1 | 9/2004 | DiBenedetto et al. |
| 2004/0186482 A1 | 9/2004 | Kolb et al. |
| 2004/0186569 A1 | 9/2004 | Berry |
| 2004/0193272 A1 | 9/2004 | Zubok et al. |
| 2004/0220571 A1 | 11/2004 | Assaker et al. |
| 2004/0254644 A1 | 12/2004 | Taylor |
| 2005/0027362 A1 | 2/2005 | Williams et al. |
| 2005/0049590 A1 | 3/2005 | Alleyne et al. |
| 2005/0177235 A1 | 8/2005 | Baynham et al. |
| 2005/0216084 A1 | 9/2005 | Fleischmann |
| 2005/0256576 A1 | 11/2005 | Moskowitz et al. |
| 2005/0261769 A1 | 11/2005 | Moskowitz et al. |
| 2005/0273170 A1 | 12/2005 | Navarro et al. |
| 2005/0278026 A1 | 12/2005 | Gordon et al. |
| 2006/0058876 A1 | 3/2006 | Laurence |
| 2006/0155285 A1 | 7/2006 | Anderson et al. |
| 2006/0241621 A1 | 10/2006 | Moskowitz et al. |
| 2007/0049943 A1 | 3/2007 | Moskowitz et al. |
| 2007/0167678 A1 | 7/2007 | Moskowitz et al. |
| 2007/0198089 A1 | 8/2007 | Moskowitz et al. |
| 2007/0213820 A1 | 9/2007 | Magerl et al. |
| 2007/0250167 A1 | 10/2007 | Bray et al. |
| 2007/0250172 A1 | 10/2007 | Moskowitz et al. |
| 2007/0276498 A1 | 11/2007 | Aebi et al. |
| 2008/0033440 A1 | 2/2008 | Moskowitz et al. |
| 2008/0177307 A1 | 7/2008 | Moskowitz et al. |
| 2008/0183293 A1 | 7/2008 | Parry et al. |
| 2008/0249569 A1 | 10/2008 | Waugh et al. |
| 2008/0249575 A1* | 10/2008 | Waugh .................... A61F 2/447 606/305 |
| 2008/0249625 A1* | 10/2008 | Waugh .................. A61F 2/4465 623/17.16 |
| 2008/0281424 A1 | 11/2008 | Parry et al. |
| 2008/0281425 A1 | 11/2008 | Thalgott et al. |
| 2009/0030520 A1 | 1/2009 | Biedermann et al. |
| 2009/0080997 A1* | 3/2009 | Johnson ............. A61B 17/8047 411/347 |
| 2009/0105830 A1 | 4/2009 | Jones et al. |
| 2009/0105831 A1 | 4/2009 | Jones et al. |
| 2009/0112271 A1 | 4/2009 | Moskowitz et al. |
| 2009/0182430 A1 | 7/2009 | Tyber et al. |
| 2009/0187218 A1 | 7/2009 | Schaffhausen et al. |
| 2009/0210062 A1 | 8/2009 | Thalgott et al. |
| 2009/0224023 A1 | 9/2009 | Moskowitz et al. |
| 2009/0234455 A1 | 9/2009 | Moskowitz et al. |
| 2010/0145460 A1 | 6/2010 | McDonough et al. |
| 2010/0305704 A1 | 12/2010 | Messerli et al. |
| 2010/0324606 A1 | 12/2010 | Moskowitz et al. |
| 2011/0125269 A1 | 5/2011 | Moskowitz et al. |
| 2011/0137349 A1 | 6/2011 | Moskowitz et al. |
| 2011/0172774 A1 | 7/2011 | Varela |
| 2011/0178600 A1 | 7/2011 | Moskowitz et al. |
| 2011/0208312 A1 | 8/2011 | Moskowitz et al. |
| 2011/0288646 A1 | 11/2011 | Moskowitz et al. |
| 2011/0295327 A1 | 12/2011 | Moskowitz et al. |
| 2011/0295371 A1 | 12/2011 | Moskowitz et al. |
| 2011/0307011 A1 | 12/2011 | Moskowitz et al. |
| 2011/0319935 A1 | 12/2011 | Moskowitz et al. |
| 2012/0010714 A1 | 1/2012 | Moskowitz et al. |
| 2012/0271423 A1 | 10/2012 | Wallenstein et al. |
| 2012/0277870 A1 | 11/2012 | Wolters et al. |
| 2012/0323330 A1 | 12/2012 | Kueenzi et al. |
| 2012/0330419 A1 | 12/2012 | Moskowitz et al. |
| 2013/0018468 A1 | 1/2013 | Moskowitz et al. |
| 2013/0018469 A1 | 1/2013 | Moskowitz et al. |
| 2013/0018470 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0060339 A1 | 3/2013 | Duffield et al. |
| 2013/0073044 A1 | 3/2013 | Gamache |
| 2013/0173002 A1 | 7/2013 | Moskowitz et al. |
| 2013/0211526 A1 | 8/2013 | Alheidt et al. |
| 2013/0282017 A1 | 10/2013 | Moskowitz et al. |
| 2014/0249629 A1 | 9/2014 | Moskowitz et al. |
| 2015/0025637 A1 | 1/2015 | Moskowitz et al. |
| 2015/0105824 A1 | 4/2015 | Moskowitz et al. |
| 2015/0148847 A1 | 5/2015 | Moskowitz et al. |
| 2016/0374830 A1 | 12/2016 | Moskowitz et al. |
| 2017/0252178 A1 | 9/2017 | Moskowitz et al. |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. To Aug. 1, 2003, pp. S15-S23.

(56) References Cited

OTHER PUBLICATIONS

Dieter Grob et al., "Clinical Experience With the Dynesys Semirigid Fixation System for the Lumbar Spine," Spine, vol. 30, No. 3, 2005, pp. 324-331.

International Search Report (ISR) and Written Opinion of the International Searching Authority, dated Dec. 3, 2007, International Application No. PCT/US 07/05005.

International Search Report (ISR) and Written Opinion of the International Searching Authority, dated May 21, 2008, International Application No. PCT/US2007/021015.

International Search Report (ISR) and Written Opinion of the International Searching Authority, dated Jul. 9, 2008, International Application No. PCT/US2007021013.

\* cited by examiner

BIDIRECTIONAL FIXATING INTERVERTEBRAL IMPLANT SYSTEM

This application is a Continuation Application of U.S. application Ser. No. 15/894,471, filed Feb. 12, 2018, which is a Continuation of U.S. application Ser. No. 13/210,157, filed Aug. 15, 2011 (now U.S. Pat. No. 9,889,022), which is a Continuation of U.S. application Ser. No. 13/084,543, filed Apr. 11, 2011 (now U.S. Pat. No. 8,353,913) and Ser. No. 13/108,982, filed May 16, 2011 (now U.S. Pat. No. 9,005,293).

U.S. application Ser. No. 13/084,543 is a Continuation of Ser. No. 11/842,855, filed Aug. 21, 2007 (now U.S. Pat. No. 7,942,903). U.S. application Ser. No. 13/108,982 is a Continuation of Ser. No. 11/842,855, filed Aug. 21, 2007 (now U.S. Pat. No. 7,942,903), which is a Continuation-in-Part of U.S. application Ser. No. 11/536,815, filed Sep. 29, 2006 (now U.S. Pat. No. 7,846,188), which is a Continuation-in-Part of U.S. application Ser. No. 11/208,644, filed Aug. 23, 2005 (now U.S. Pat. No. 7,704,279), which claims priority of U.S. Provisional Application Ser. No. 60/670,231, filed Apr. 12, 2005; the entire contents of all the above identified patent applications are hereby incorporated by reference.

FIELD OF INVENTION

The present invention relates to a unique universal bidirectional screw (BDS) system, and in particular its application to the spine, also referred to as bi-directional fixating transvertebral (BDFT) screws which can be used as a stand-alone intervertebral device which combines the dual functions of an intervertebral spacer which can be filled with bone fusion material(s), as well as a transvertebral bone fusion screw apparatus. In the posterior lumbosacral and thoracic spine, BDFT screw/box constructs can be used independently or supplemented with a novel horizontal mini-plate which prevents upward bone graft intrusion into the thecal sac and nerves. In the anterior lumbosacral spine BDFT screw box constructs can be inserted into and supplemented by a circumferential cage. These posteriorly and anteriorly placed stand-alone intervertebral body fusion constructs may obviate the need for supplemental pedicle screw fixation.

The present invention also relates to stand-alone or supplemental posterior cervical and lumbar calibrated interarticular joint stapling devices which may obviate and/or lessen the need for supplemental pedicle screw fixation.

DESCRIPTION OF THE RELEVANT ART

The history and evolution of instrumented spinal fusion in the entire human spine has been reviewed in our two prior copending application Ser. No. 11/536,815, filed on Sep. 29, 2006, and Ser. No. 11/208,644, filed on Aug. 23, 2005, the related contents of which are hereby incorporated by reference. Currently the majority of posterior cervical and almost all anterior and posterior lumbosacral and thoracic fusion techniques are typically supplemented with pedicle screw placement. Complications of pedicle screw placement in cervical, thoracic and lumbar spine include duration of procedure, significant tissue dissection and muscle retraction, misplaced screws with neural and/or vascular injury, excessive blood loss, need for transfusions, prolonged recovery, incomplete return to work, and excess rigidity leading to adjacent segmental disease requiring further fusions and re-operations. Recent advances in pedicle screw fixation including minimally invasive and image-guided technology, and the development of flexible rods, imperfectly address some but not all of these issues.

Complications of all current spinal interbody fusion devices is their lack of coverage of the majority of the cross-sectional area of the vertebral endplates, and their lack of adequate, if any capacity to penetrate bone, and hence the heightened risk of implant extrusion. Furthermore the bone and biological bone fusion agents which are packed into the intervertebral space can easily blossom and grow upward into the thecal sac causing neural compression, in the absence of a physical barrier between the fusing growing bone, and the thecal sac.

SUMMARY

Herein we describe multiple device embodiments which combine in a single construct the dual functions of an intervertebral spacer maintaining disc space height, and transvertebral body fusion screws.

We also introduce an entirely novel horizontal mini-plate capping off the intervertebral space capable of functioning as a physical barrier preventing upward bone intrusion and/or compression of the ventral thecal sac, and traversing and exciting nerve roots.

Furthermore, we present an advanced mechanism in calibrated posterior facet joint stapling compared to our previous designs illustrated in our co-pending patents. We also introduce the entirely novel concept of posterior cervical facet staples to obviate and/or diminish the need for posterior cervical pedicle screw instrumented fusion. Using combinations and permutations of different embodiments of cervical facet staples in a modular manner advances the concept of flexible fusion in the cervical spine.

To achieve safe, effective and minimally invasive segmental spinal fusion, applicants propose the use of novel bi-directional fixating transvertebral (BDFT) screws which can be strategically inserted via anterior or posterior surgical spinal approaches into the anterior and middle columns of the interverterbral disc space. In our previous applications these bi-directional screws employed turning a wormed driving screw which turns a spur gear which in turn simultaneously turns a rostral oriented screw into the cephalad vertebral body, and a caudal directed screw into the caudal vertebral body. The vertebral bodies above and below the disc space by virtue of their engagement and penetration by the BDFT screws are thus linked, interlocked, and eventually biologically fused with placement of intervertebral bone agents.

In this current application one or more of the described embodiments may eliminate the intervening wormed driving screws and gears required by previous designs, e.g., a gearless screw box is achieved. We have designed a screw box to be placed inter-vertebrally, either unilaterally or bilaterally, in particular, posteriorly between vertebral bodies. The housing screw box incorporates built-in screw and/or drill guides which allow the direct placement and insertion of two self drilling screws which are driven in two opposing directions into superior and inferior vertebral bodies, respectively. One screw within the screw box is angled superiorly, and the other screw in the screw box is angled inferiorly.

In yet another embodiment, in addition to these features we designed an expanding screw box with sliding triangular bases to house two screws driven in two opposing directions which can be expanded in two simultaneous directions, height and depth, by turning a built-in screw adjuster. This is accomplished by a combined positioning tool/screw guide/cage expander to further enhance trajectory precision and to simultaneously expand the screw box in height and depth to custom-fit the individual disc space height. This embodiment has two sub-embodiments; one has two laterally oriented BDFT screws, and the other has a lateral and a medial oriented BDFT screw. These innovations represent a continued evolution of our concept of expandable fusion cages described in our previous co-pending patents.

In yet another embodiment we designed a screw box which houses only one, instead of two screws. Each box allows the placement of one superior or inferior directed screw on one side (left or right), and the contra lateral screw box device allows placement of an inferior or superior oriented screw which goes in the opposite direction of the contra lateral device. In totality these two separate single screw boxes fuse the superior and inferior vertebrae. The potential advantage of this embodiment is that it diminishes the width of the screw box in cases where it might be favorable to have less nerve root retraction with a smaller width device.

In all screw-box embodiments, a rostral-directed screw is passed through one built-in screw guide of the device which then is inserted and screwed into the superior vertebral body. Then a caudaly directed screw is passed through an adjacent built-in screw guide which then is inserted and screwed into the inferior vertebral body. The novelty of this design is the built-in prescribed angles of the integral screw guides which allow the posterior transvertebral penetration into the vertebral bodies. This is a truly amazing feat accomplished in the posterior lumbar spine considering the small anatomically restricted work zone within which to work, which is very narrowly prescribed by obtuse angulations between screw and intervertebral bone surfaces, and by nerve root, facet joint and pedicle. We have also designed a positioning tool for the placement of the non-expandable screw boxes which has a screwdriver with a flexible shaft specifically designed to fit these devices if a straight screw driver impedes screw placement. Hence these external tools provide the means in any circumstance to accomplish precision screw trajectory. The embodiments described herein compared to our previous co-pending patent designs, streamline and ease production of bi-directionally oriented transvertebral screws, and allows placement of longer and wider screws with greater bone penetration to provide yet a sturdier fusion construct. The designs are also easily modifiable for anterior placement into the cervical spine. The expandable embodiment of the screw box can also be enlarged and modified to be suitable for cervical, thoracic and lumber vertebral body replacements.

The box casings have multiple perforations to allow both screw traversal and horizontal bone packing preventing upward vertical migration of bone. The boxes prevent subsidence. Both the inside of the denuded intervertebral space, and the screw boxes can be packed with autologous or allograft bone, BMP, DBX or similar osteoconductive material. Posteriorly or anteriorly in the lumbar spine, these screws can be capped with a horizontal mini-plate which will prevent bony growth into the thecal sac and nerves. We refer to this as a two-in-one device, i.e. two screw boxes/BDFT screws combined with one horizontal mini-plate. This is an entirely novel concept in posterior lumbar spinal surgery. In yet another embodiment two BDFT screw boxes can be combined with a circumferential cage (also 2 in 1) to be placed anteriorly into the lumbar spine.

It is believed that BDFT-screw constructs provide as strong or stronger segmental fusion as pedicle screws without the complications arising from pedicle screw placement which include screw misplacement with potential nerve and/or vascular injury, violation of healthy facets, possible pedicle destruction, blood loss, and overly rigid fusions. By placing screws across the intervertebral space from vertebral body to vertebral body, engaging anterior and middle spinal columns, and not the vertebral bodies via the transpediclar route, the healthy facet joints, if they exist, are preserved. Because this technique accomplishes both anterior and middle column fusion, without rigidly fixating the posterior column, it in essence creates a flexible fusion. This device therefore is a flexible fusion device because the preserved posterior facet joints retain their function achieving at least a modicum of mobility and hence a less rigid (i.e. a flexible) fusion.

The very advantage of transpedicular screws which facilitate a strong solid fusion by rigidly engaging all three spinal columns is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral screw box embodiments and BDFT screws can be introduced via posterior lateral, transforaminal or anterior interbody fusion approaches/techniques. Although one can opt to supplement these screws with transpedicular screws there would be no absolute need for supplemental pedicle screw fixation with these operative techniques.

BDFT screw constructs outlined here can also be combined with novel zero-profile horizontal cervical and, lumbar/thoracic mini-plates. Likewise one or two of these devices can be inserted anteriorly with or without circumferential cage supplementation.

Because the BDFT screws engage a small percentage of the rostral and caudal vertebral body surface area, multi-level fusions can be performed with these devices.

Previous improvements included a novel calibrated lumbar/thoracic facet stapling device which staples the inferior articulating facet of the superior segment to the superior articulating facet of the caudal vertebral segment unilaterally or bilaterally, which may minimize motion until interbody fusion occurs. In the present patent application we introduce a new design of the staple enhancing its calibrating capability.

In this patent application we also introduce a novel posterior cervical facet stapling device which staples the inferior articulating facet of the superior cervical segment with the superior articulating facet of the caudal vertebral segment unilaterally or bilaterally.

The advantage of cervical facet staples is speed and safety. The risks of cervical facet pedicle screw fixation which include nerve root and vertebral artery injuries are completely obviated. Thus they thereby achieve the same function of pedicle screws without the risks.

Placement of different embodiments of the cervical facet staples along unilateral and/or bilateral facet joints in a modular manner, lead to differing degrees of calibrated motion joint motion hence introducing for the first time the concept of calibrated cervical fusion.

Currently failed anterior lumbar arthroplasties are salvaged by combined anterior and posterior fusions. BDFT screw constructs could be utilized as a one-step salvage operation for failed/extruded anteriorly placed lumbar artificial discs obviating the above salvage procedure which has far greater morbidity.

For example, in one general aspect, a self-drilling bone fusion screw apparatus includes a first sliding box, a second sliding box, positioned relative to the first sliding box, a first screw member having a tapered end and a threaded body disposed within the first sliding box, a second screw member having a tapered end and a threaded body disposed within the second sliding box, and an adjuster for adjusting the height of the sliding boxes.

Implementations of this aspect may include one or more of the following features. For example, the first and second screw members may be medially aligned. At least one of the first and second screw members may be laterally aligned. The first and second screw members are laterally aligned. One of the first and second screw members is laterally aligned and the other screw member is laterally aligned. The first and second sliding boxes may be substantially triangularly shaped. The triangularly shaped first and second sliding boxes may include a sliding rail and ridged surfaces. The triangularly shaped first and second sliding boxes may include holes for bone grafts. The adjuster may include a screw.

In another general aspect, a self-drilling bone fusion screw apparatus includes a box, a first screw member having a tapered end and a threaded body disposed at least partially within the box and laterally aligned with the box, a second screw member having a tapered end and a threaded body disposed at least partially within the box and laterally aligned with the box, and a plurality of ridges disposed on along the sides of the box.

Implementations of this aspect may include one or more of the following features. For example, the apparatus may include bone graft holes. The apparatus may be attachable to a second self-drilling fusion screw apparatus via a plate.

In another general aspect, a self-drilling bone fusion screw apparatus may include a first box, a first screw member having a tapered end and a threaded body disposed at least partially within the first box and laterally aligned with the first box, a second box, a second screw member having a tapered end and a threaded body disposed at least partially within the second box and laterally aligned with the second box, and an attachment member for engaging the first and second boxes.

Implementations of this aspect may include one or more of the following features. For example, the self-drilling bone fusion screw apparatus may include bone graft holes. The plate may be directly joined to the first and second boxes by a plurality of screws. The attachment member for engaging the first and second boxes may include a plate or the attachment member may include a circumferential cage defining at least one recess. The first and the second boxes may be positioned within or securely held within the recess of the circumferential cage, e.g, with an interference fit.

In another general aspect, a tool assembly for manipulating a self-drilling bone fusion screw apparatus includes a handle, a gripper cooperating with the handle and having a plurality of prongs, a screw guide, held in place the plurality of prongs, for controlling the direction of self-drilling screws that are screwed into a vertebral body.

Implementations of this aspect may include one or more of the following features. For example, the tool assembly for manipulating a self-drilling bone fusion screw apparatus may include a key for controlling an adjustment device which controls the height of the self-drilling bone fusion screw apparatus. The tool assembly according to claim may include a driver assembly. The driver assembly may include a handle, a drive bit portion, and a flexible drive shaft extending between the handle and the drive bit portion for manipulating a screw of an expandable or non-expandable screw box. The assembly may include one or more of an expandable screw box and/or a non-expandable screw box. The boxes may include one or more screws. The screw boxes may be joined by or include an attachment member, such as a plate and/or a circumferential cage.

In another general aspect, a cervical facet staple includes a curved staple base, at least two prongs attached to the bottom surface of the curved staple base, and an insertion member disposed on the top surface of the curved staple base.

Implementations of this aspect may include one or more of the following features. For example, the staple may include at least four prongs attached to the bottom surface of the curved staple base. The insertion member may include a threaded insert.

In another general aspect, an impaction tool for a cervical facet staple includes a handle, a stem attached to the handle, a plurality of wings for contacting the cervical facet staple, and an insertion member for coupling the cervical facet staple to the impaction tool.

Implementations of this aspect may include one or more of the following features. For example, the handle may include a flattened portion that can be struck by a mallet.

In another general aspect, a lumbar facet staple includes a pair of rotating arms, at least two prongs attached to the inner surfaces of the rotating arms, a plurality of spurs attached to one of the rotating arms, and a ratchet attached to one of the rotating arms. The rotating arms and prongs are rotated to a closed position to staple a lumbar facet joint.

FIGS. E-G illustrate the sequential steps (I-III) of the positioning tooll/screw guide/box expander assembly. Step I (FIG. 5E), step II (FIG. 5F), and step III (FIG. 5G).

Figure 5A:
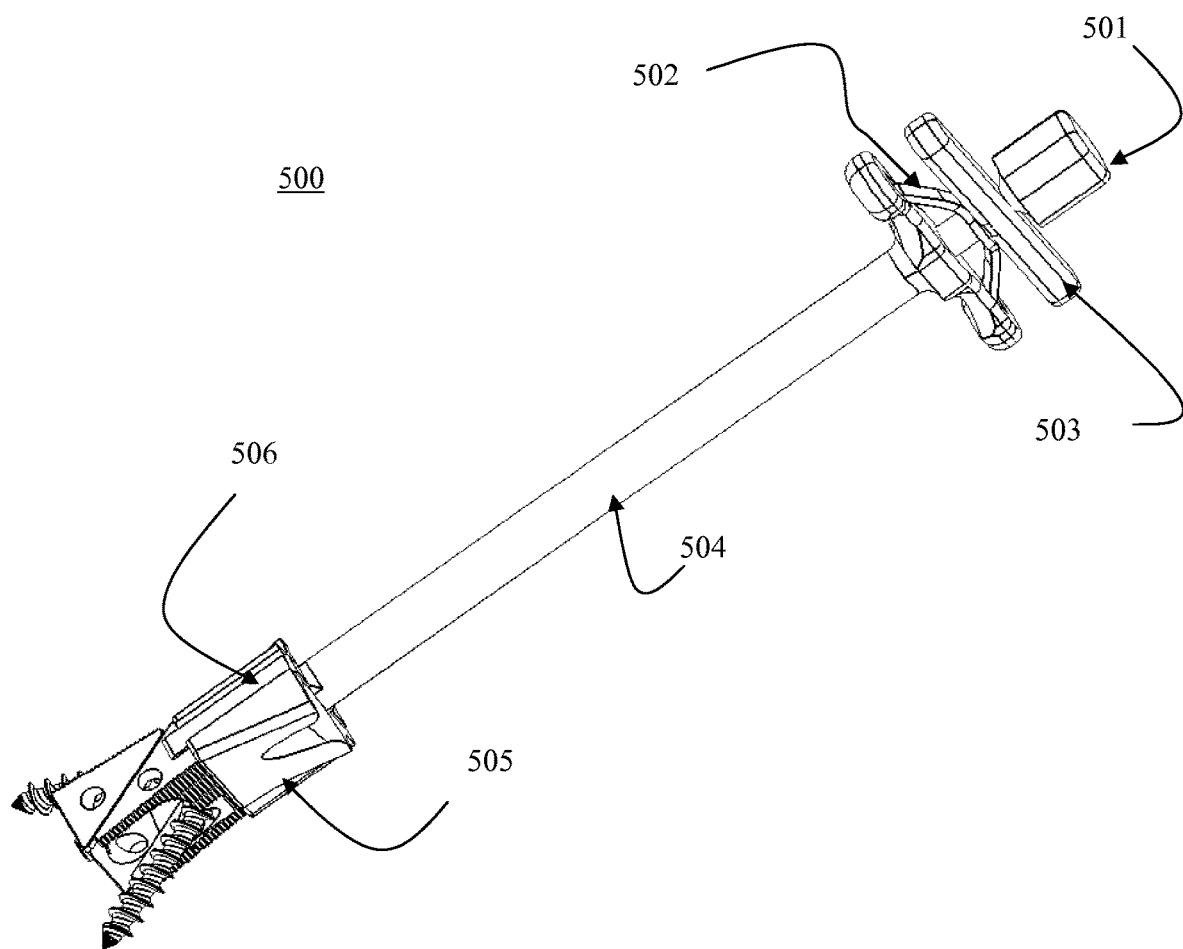
FIGS. 5A-C illustrate t positioning tool/screw guide/box expander in oblique perspective (FIG. 5A), lateral (FIG. 5B), and exploded (FIG. 5C) views.
Figure 5B:
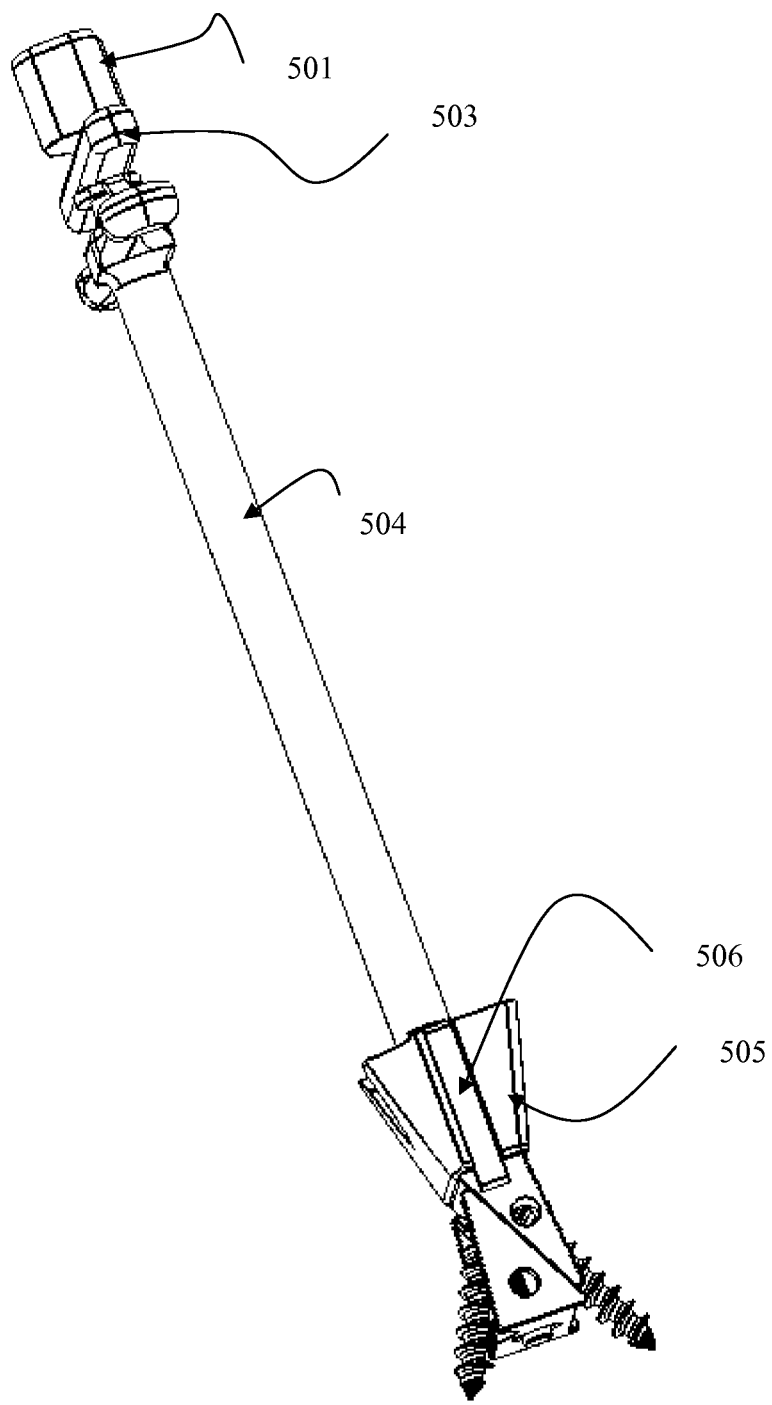
Figure 5C:
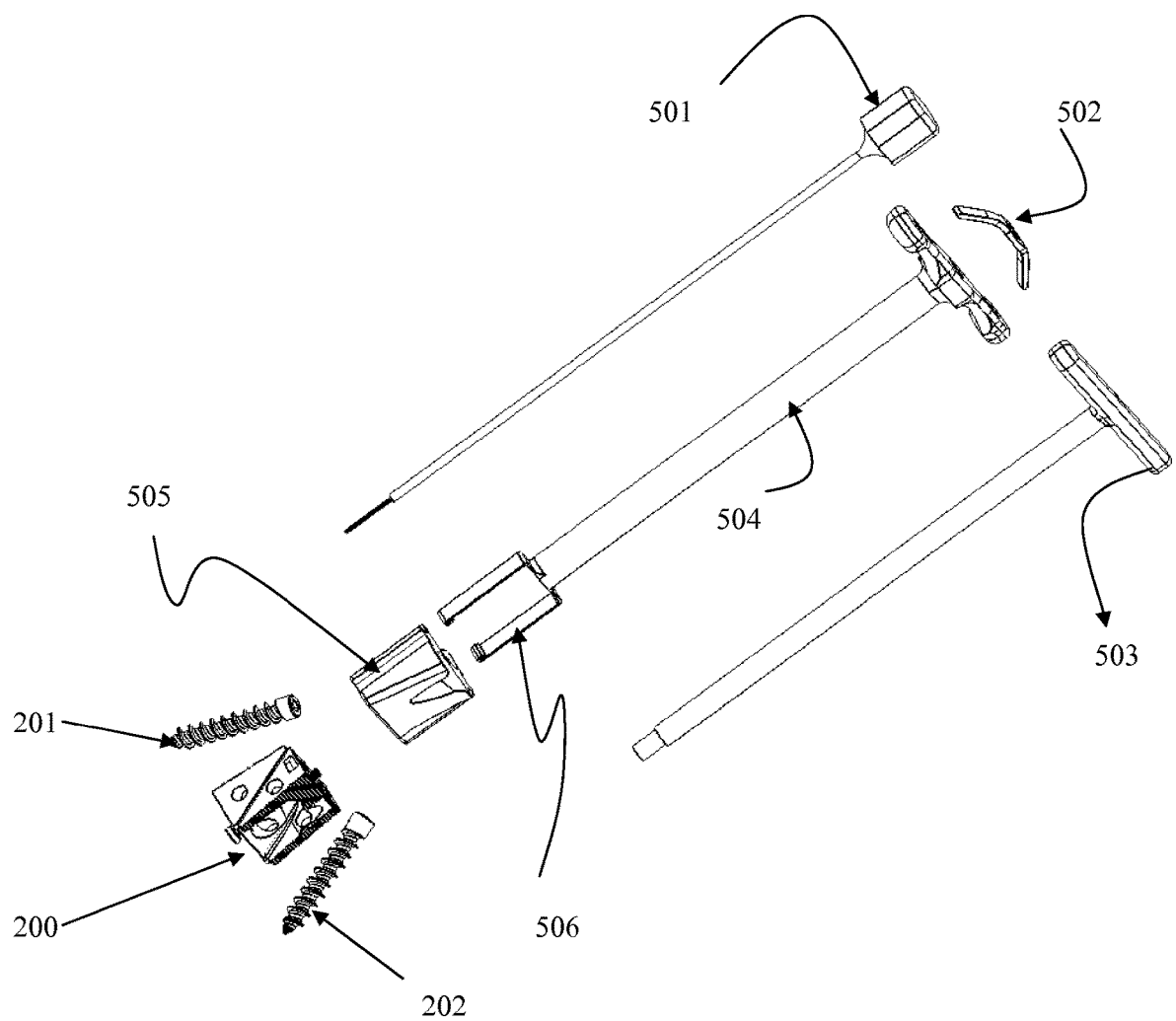
Figure 5D:
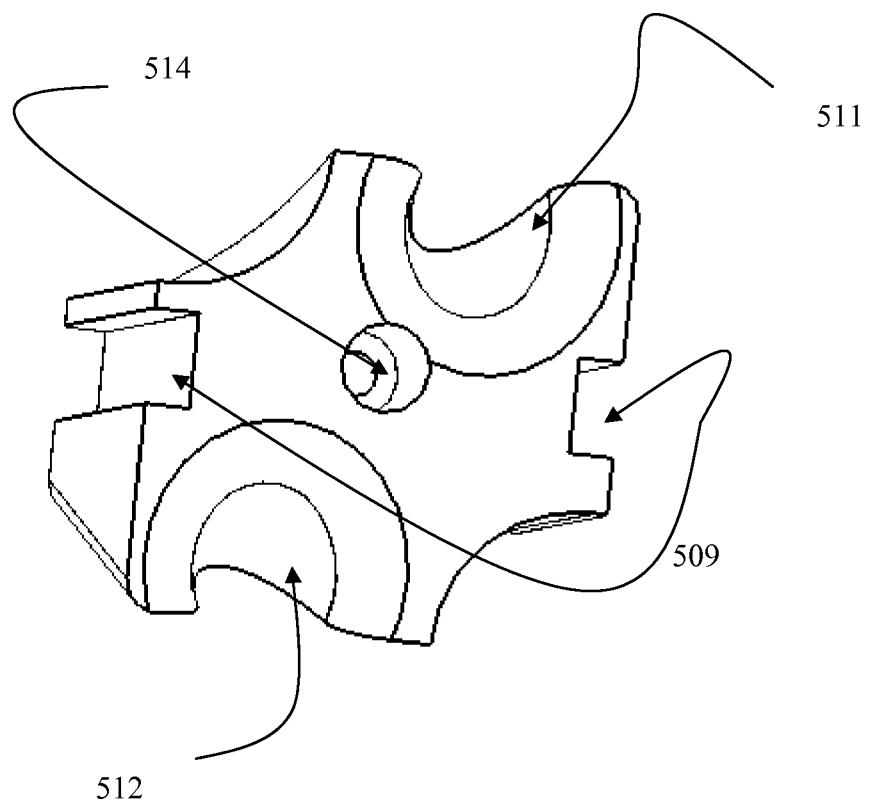
FIG. 5D illustrates a superior oblique perspective view of the positioning tool/drill guide/box expander component.
Figure 5E:
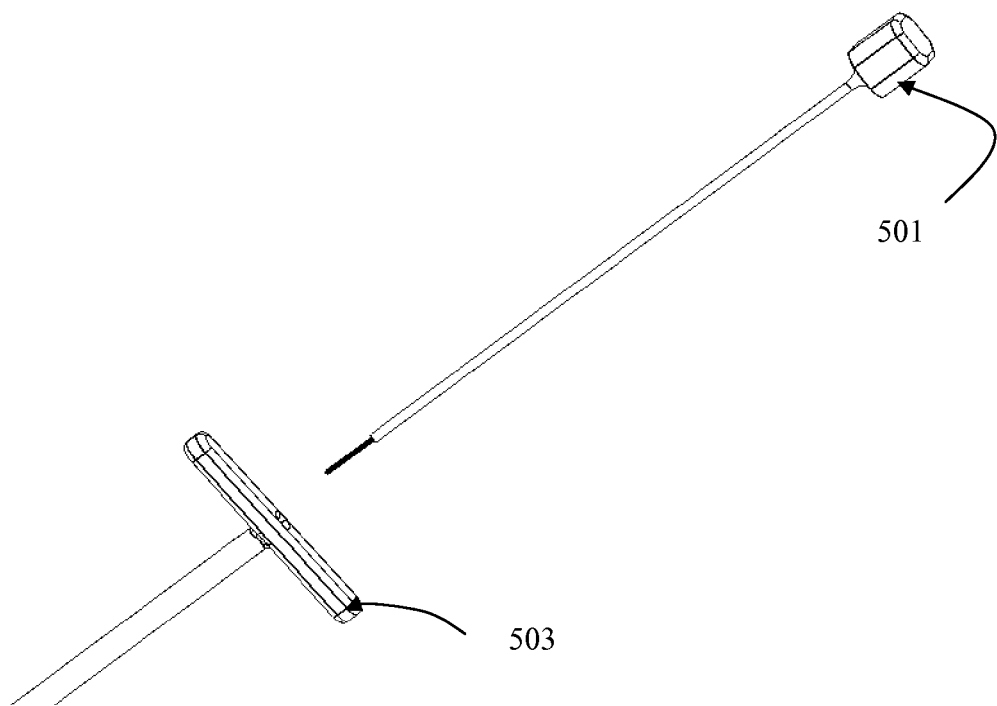
Figure 5F:
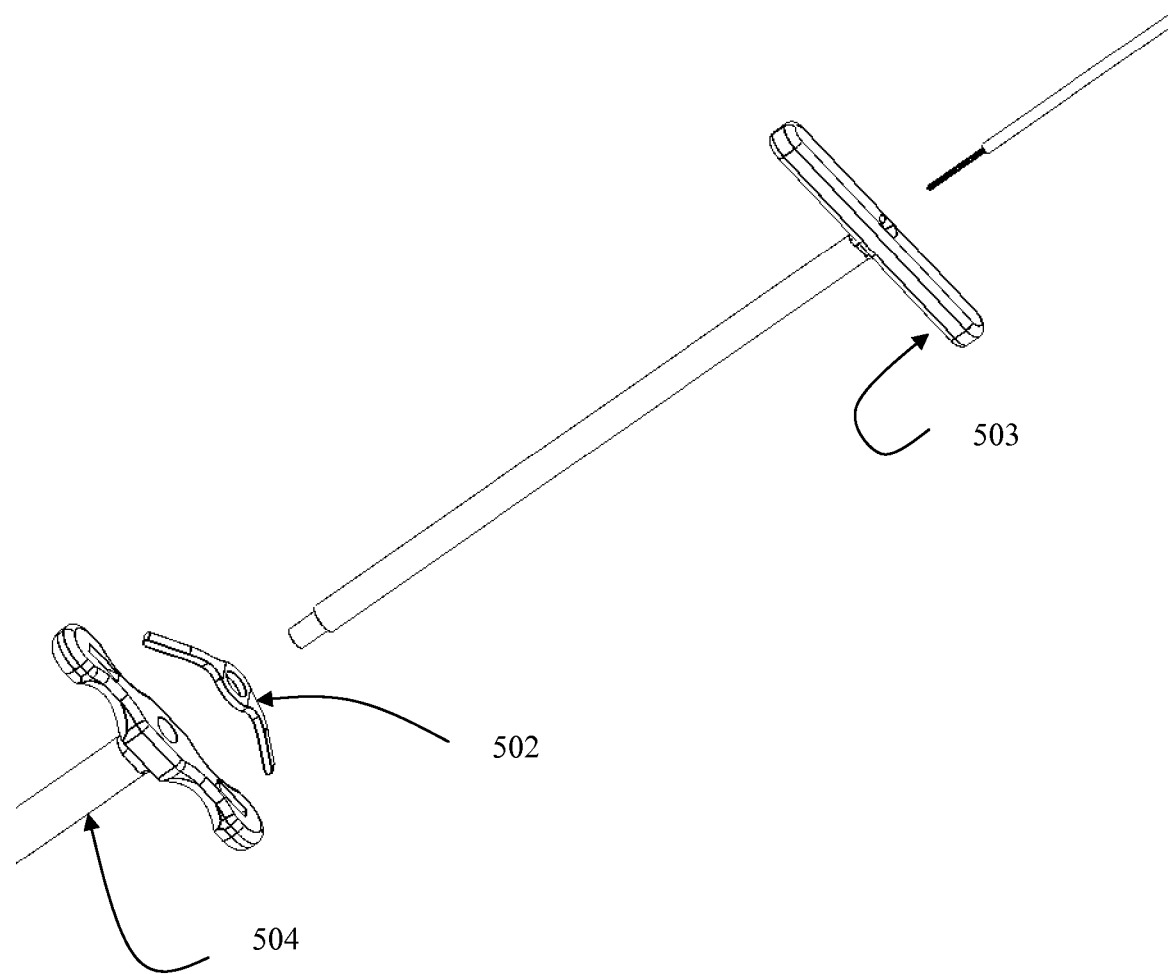
Figure 5G:
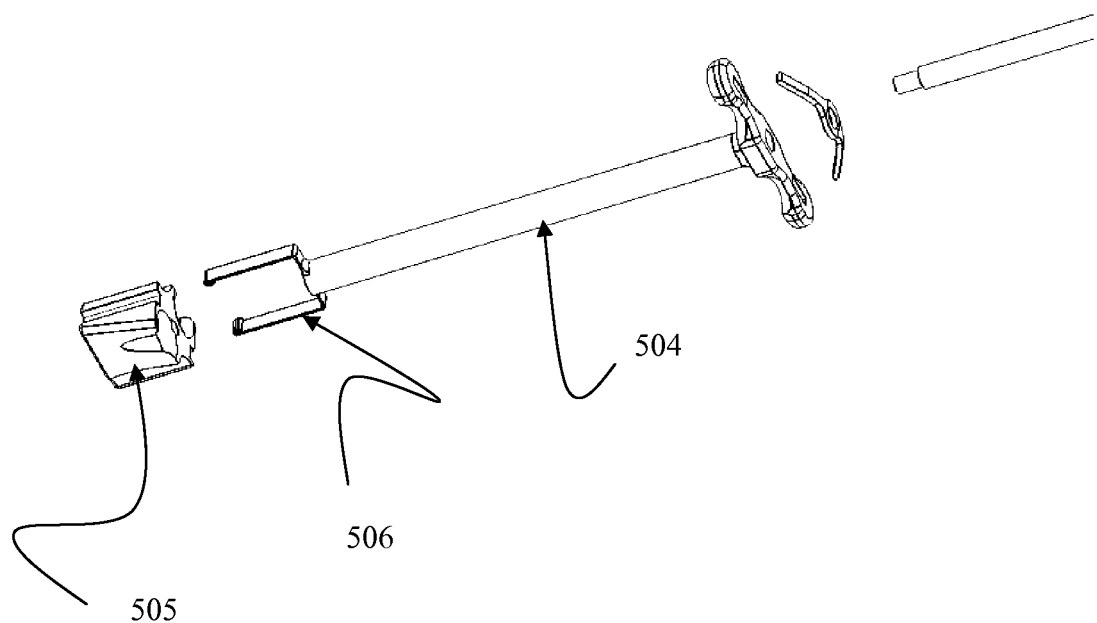
Figure 5H:
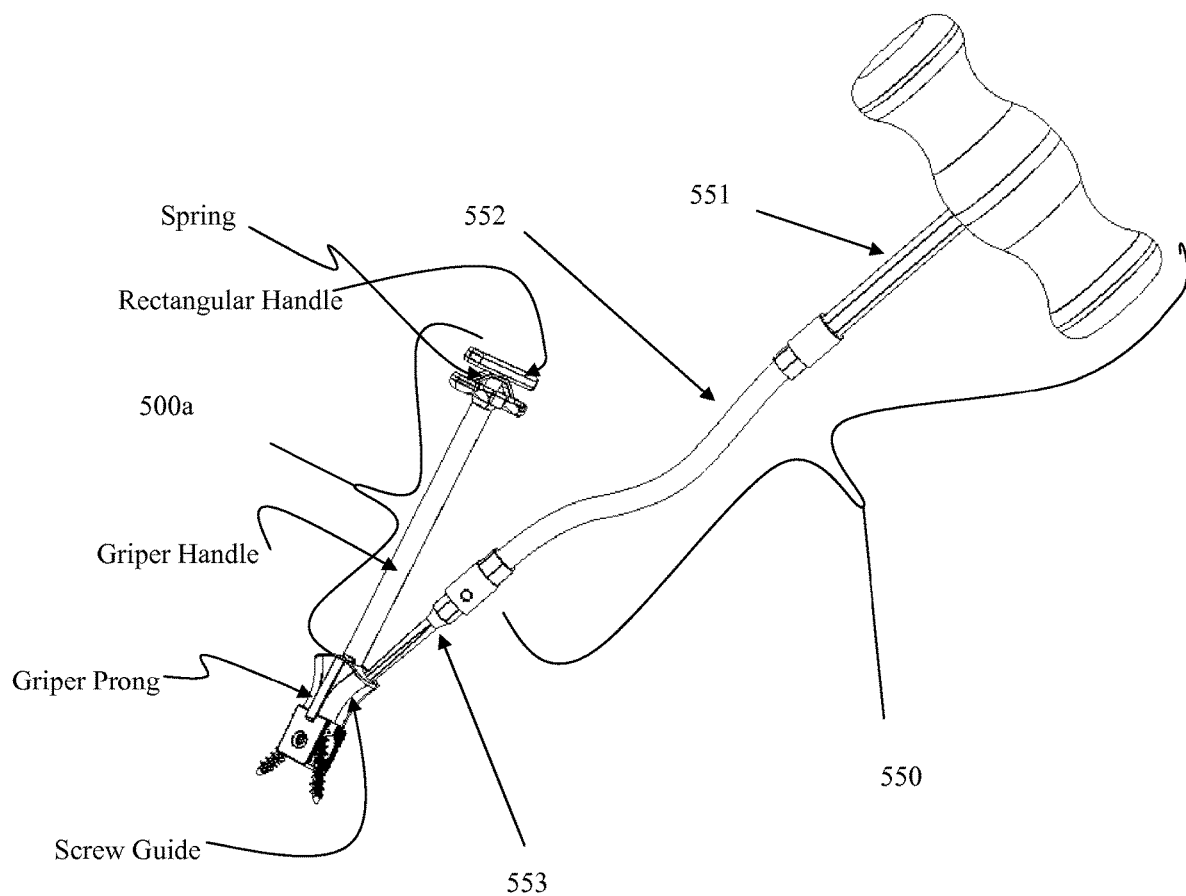
Figure 5I:
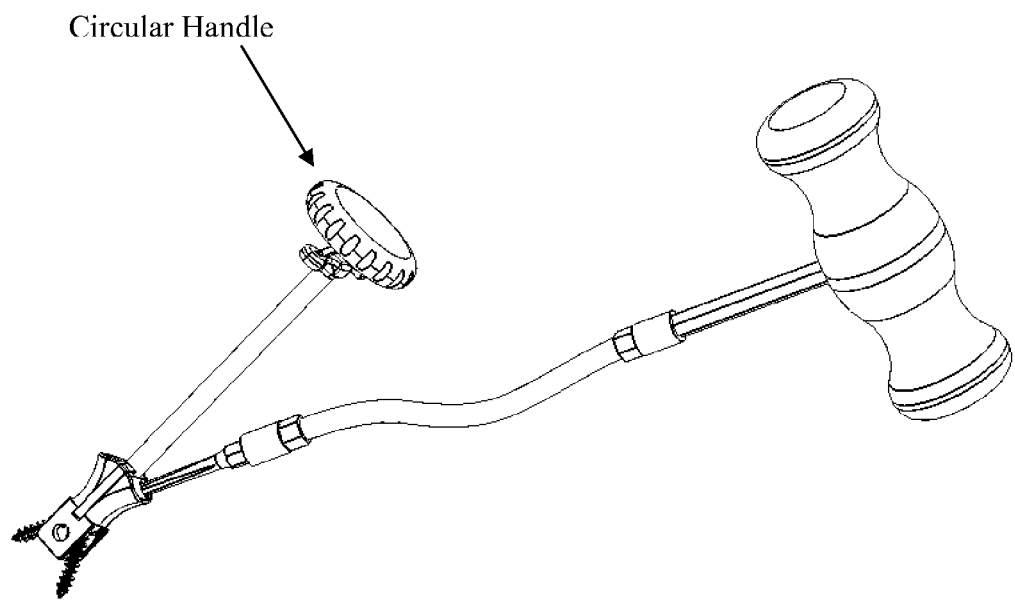

FIGS. 5H-I illustrate the positioning tool for impaction and placement of the non-expandable screw box with two transvertebral screws. Embodiment I has a rectangular positioning handle (FIG. 5H), and embodiment II has a circular positioning handle (FIG. 5I)

Figure 6A:
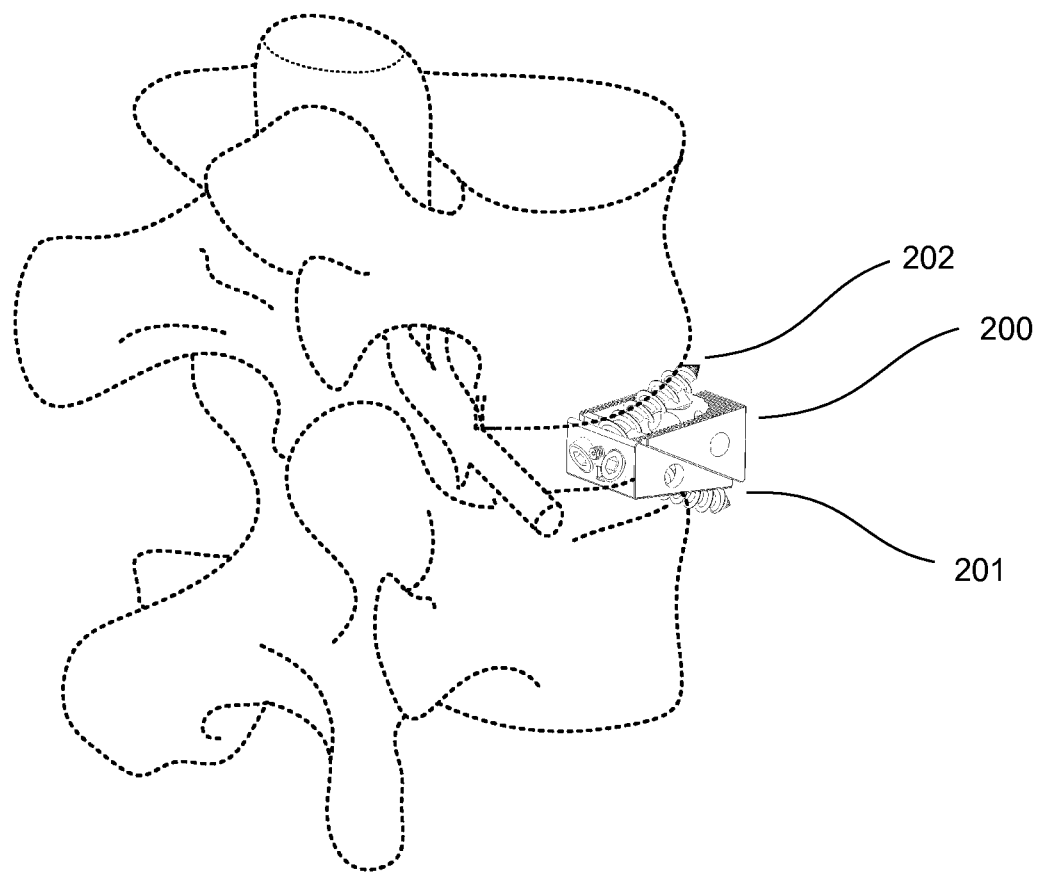
Figure 6B:
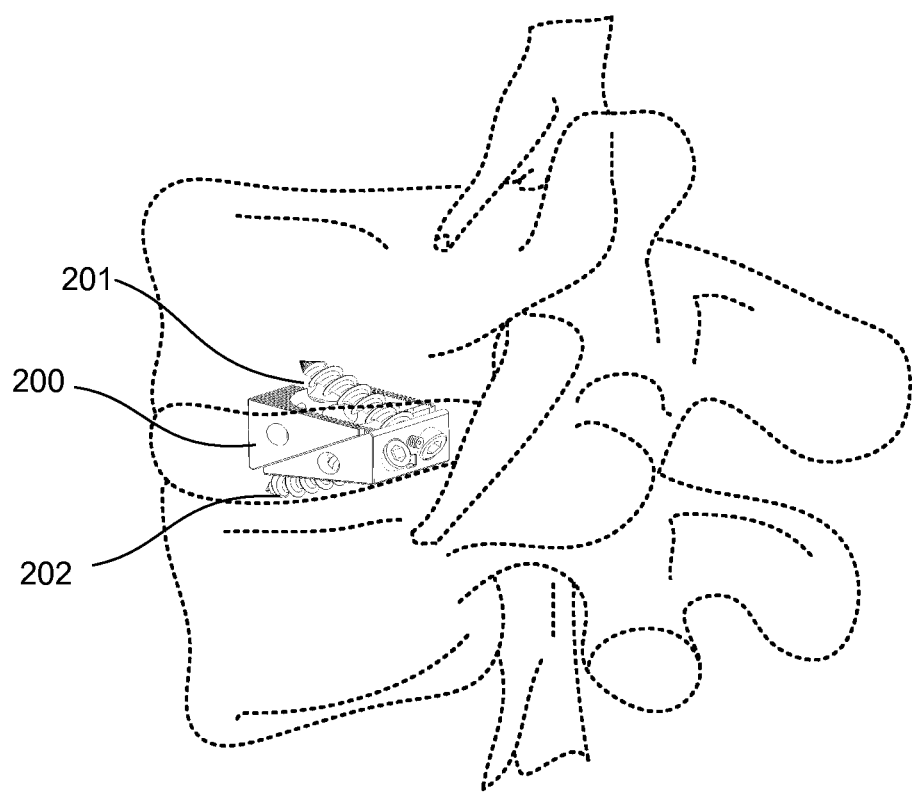

FIGS. 6A-B illustrate the insertion of expandable Lumbar bi-directional screw box with two BDFT screws into the Lumbar spine in oblique (FIG. 6A) and lateral (FIG. 6B) views.

Figure 7A:
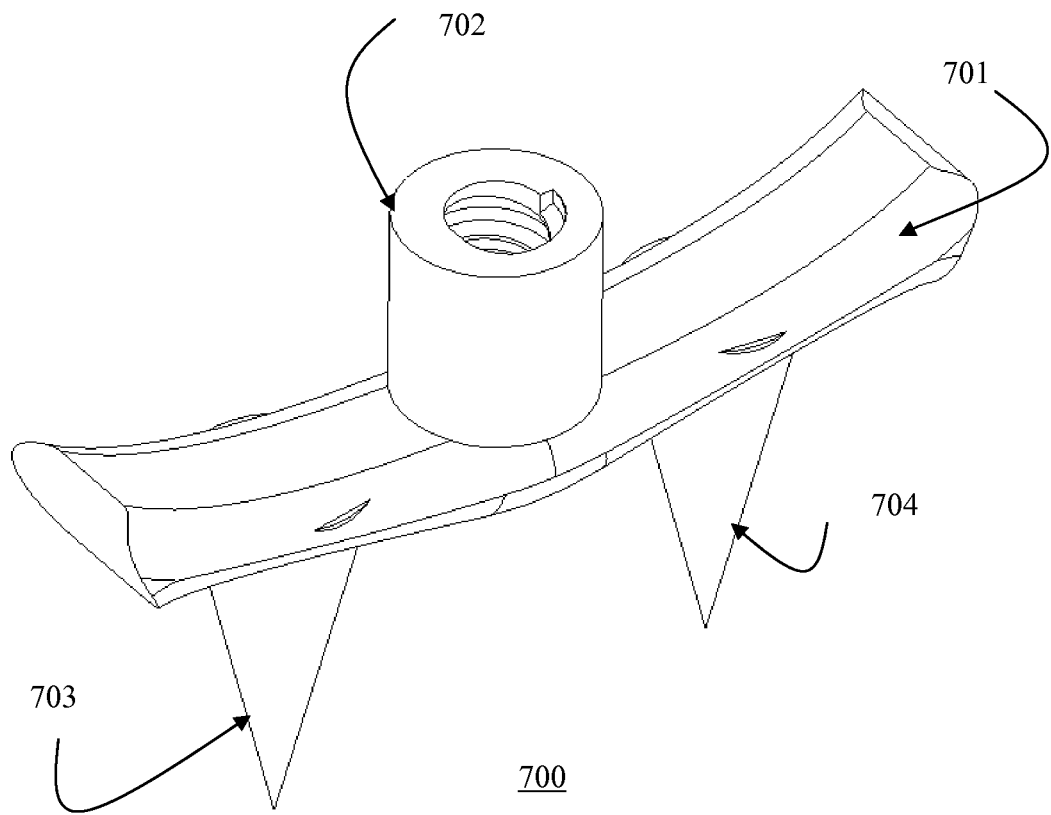
Figure 7B:
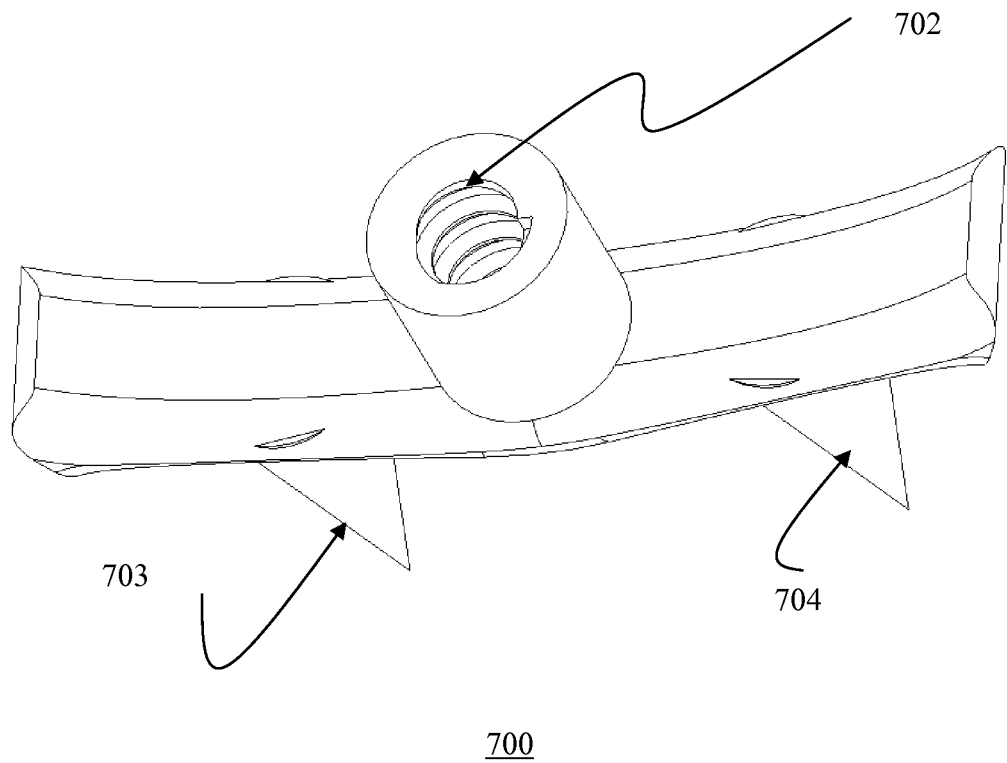

FIGS. 7A-B illustrate the cervical facet staple (Embodiment I) in lateral (FIG. 7A) and oblique (FIG. 7B) views.

Figure 8A:
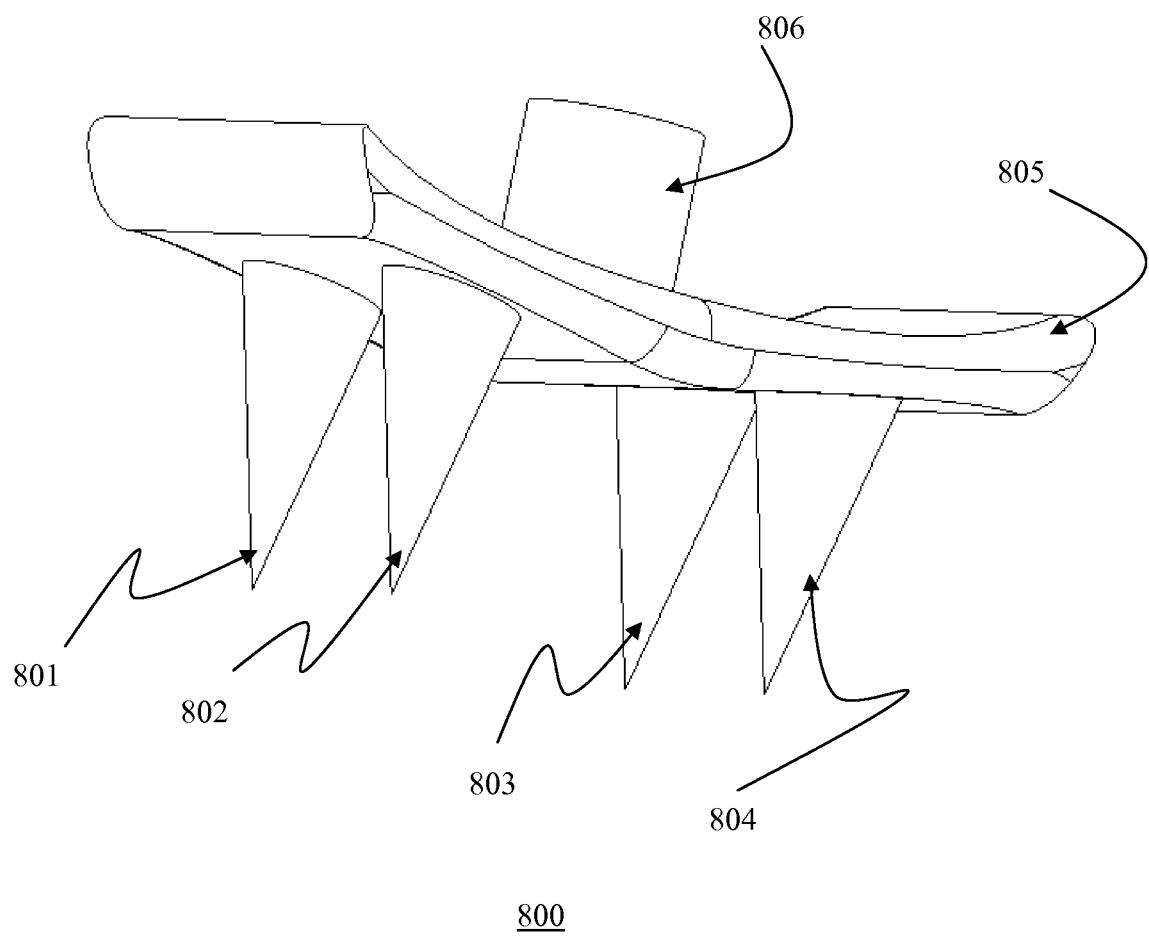
Figure 8B:
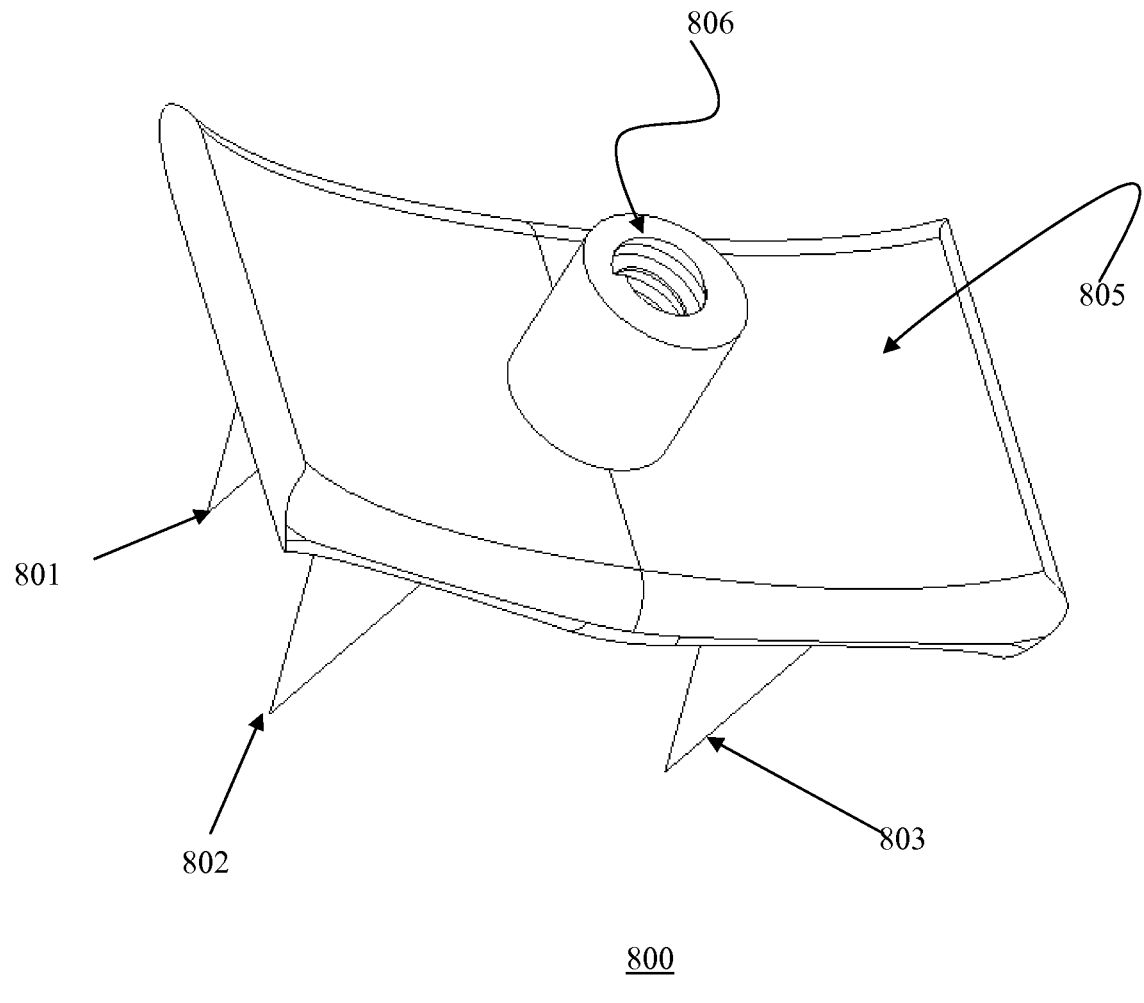
Figure 8C:
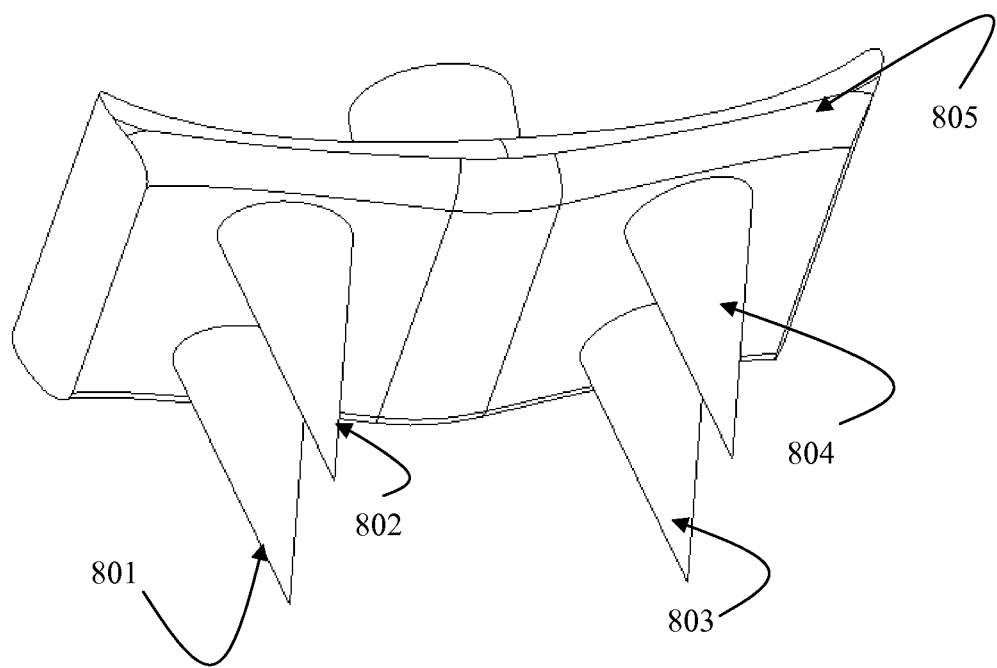

FIGS. 8-C illustrate the cervical facet staple (Embodiment II) in oblique (FIG. 8A), superior perspective (FIG. 8B) and inferior-oblique (FIG. 8C) views.

Figure 9A:
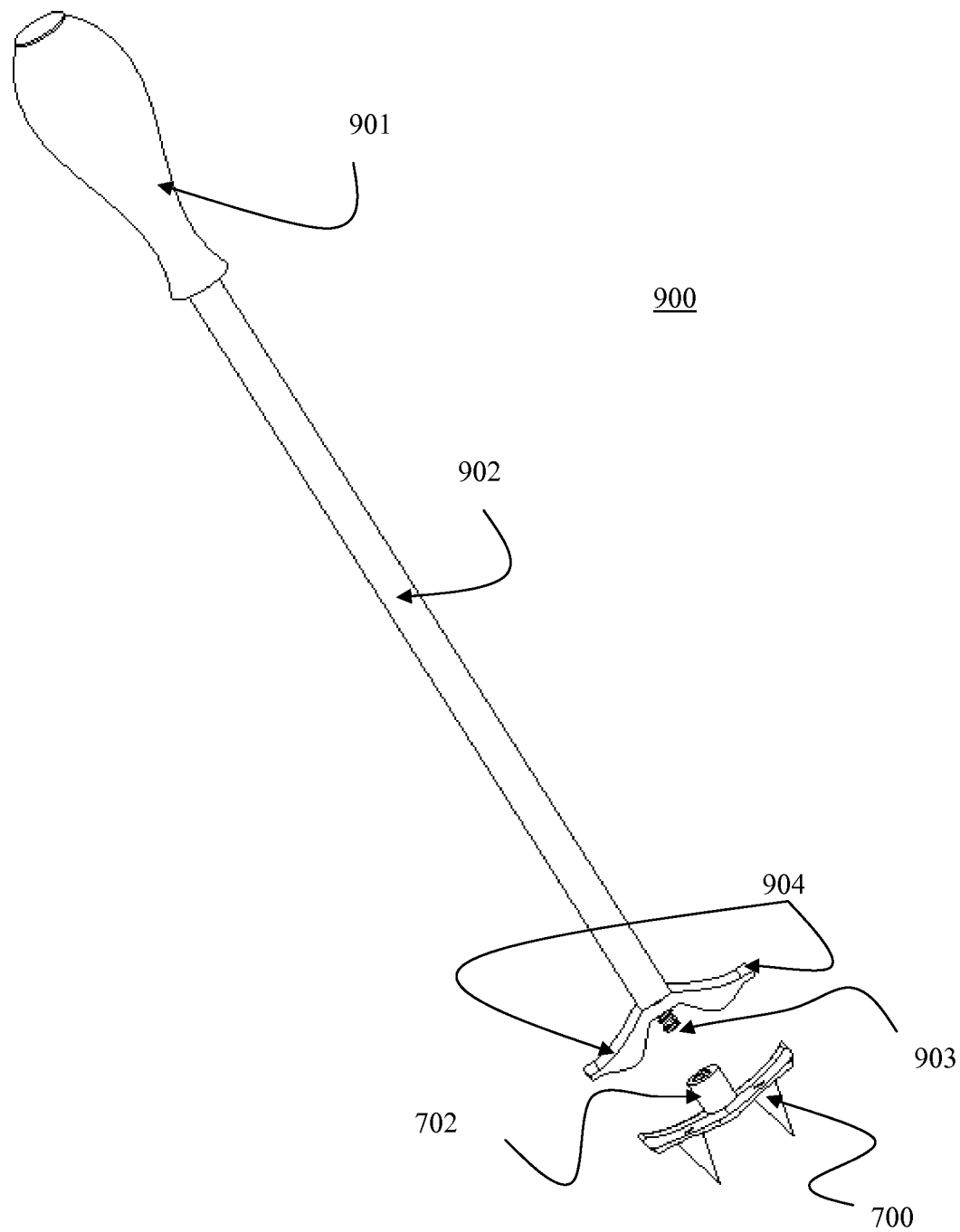

FIG. 9A illustrates the two-pronged cervical facet staple inserter/impactor (Embodiment I).

Figure 9B:
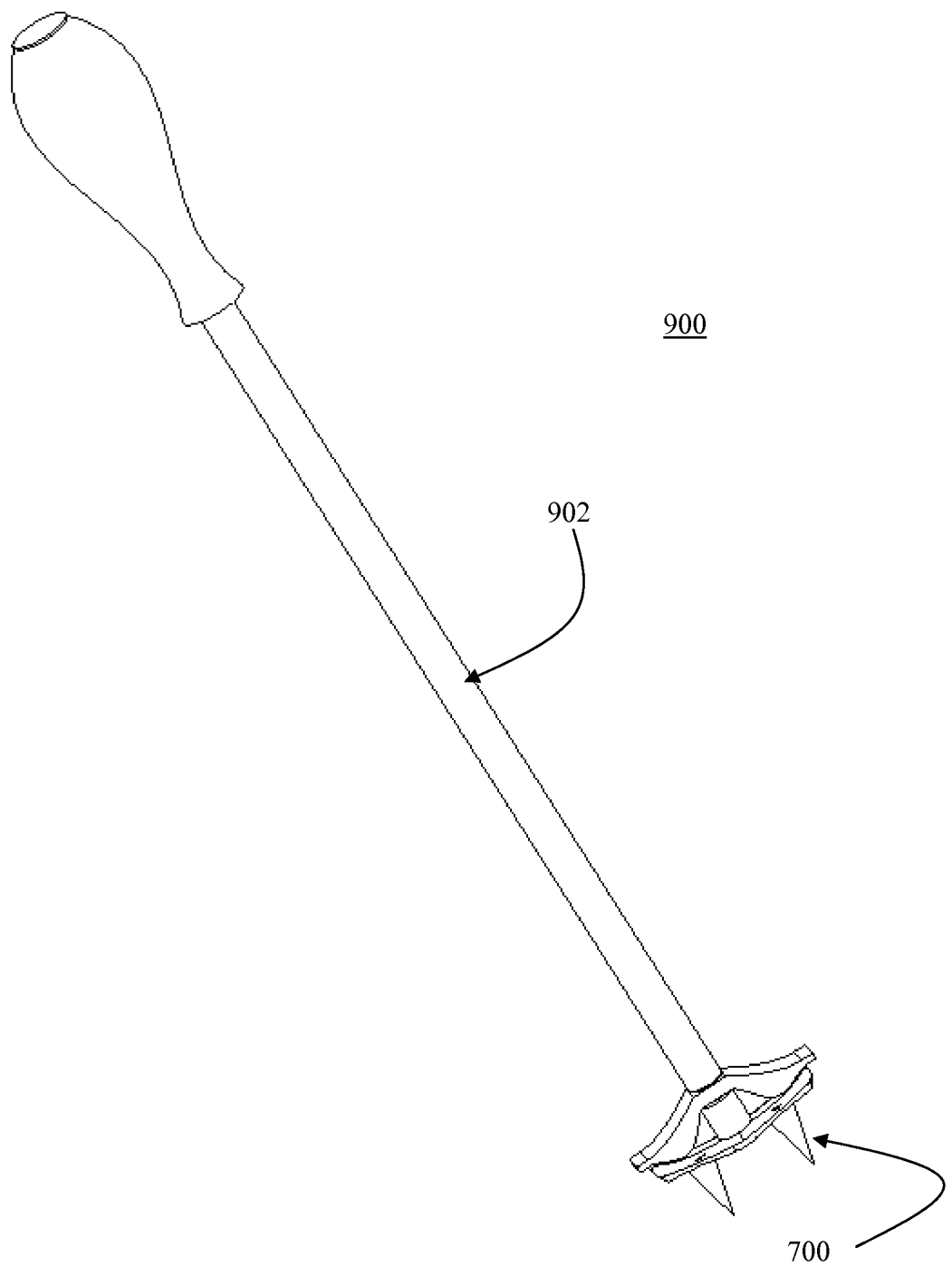

FIG. 9B illustrates the two-pronged cervical facet staple inserter/impactor inserted into the staple (Embodiment I).

Figure 10A:
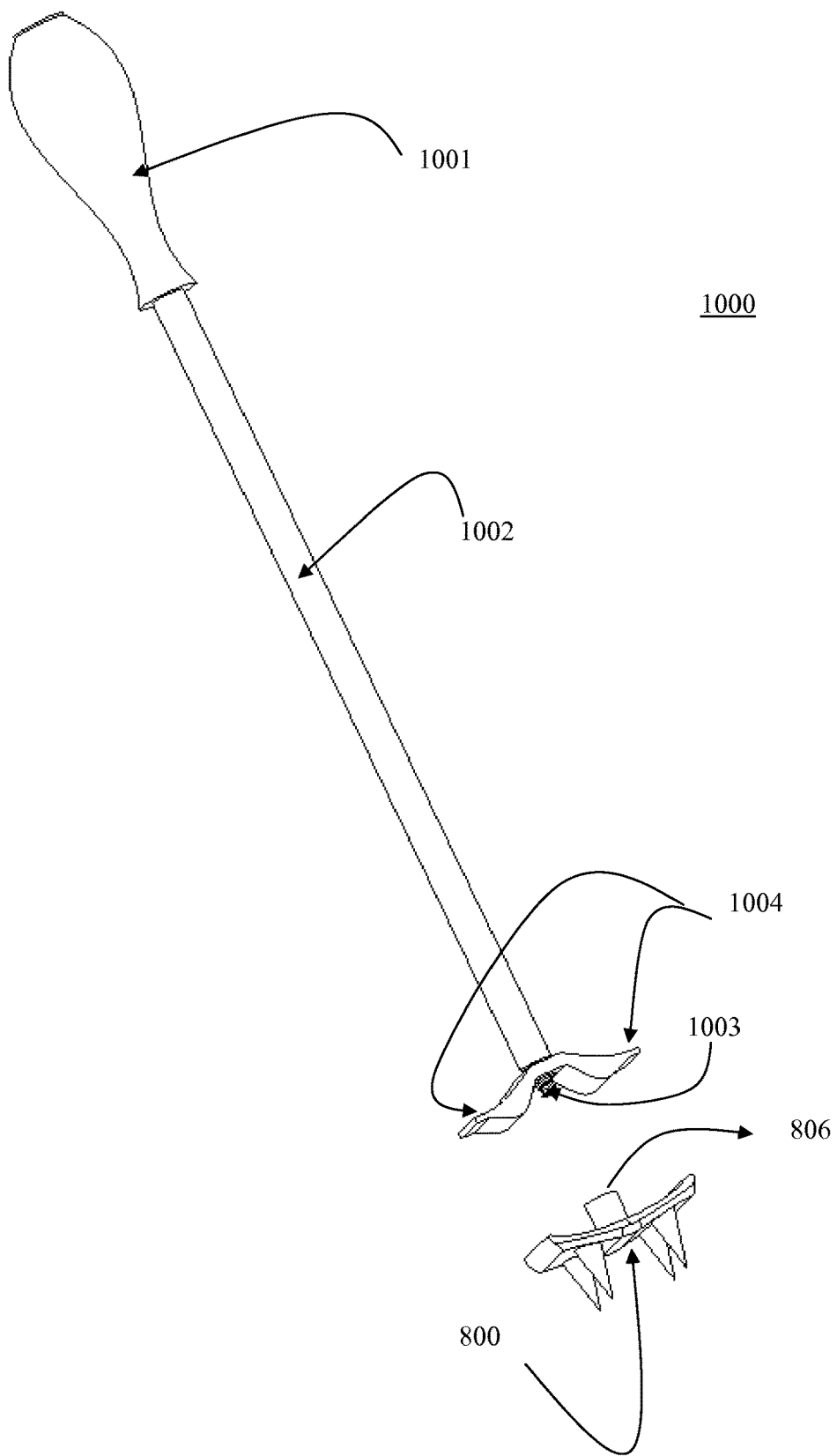

FIG. 10A illustrates the four pronged cervical facet staple impactor (Embodiment II).

Figure 10B:
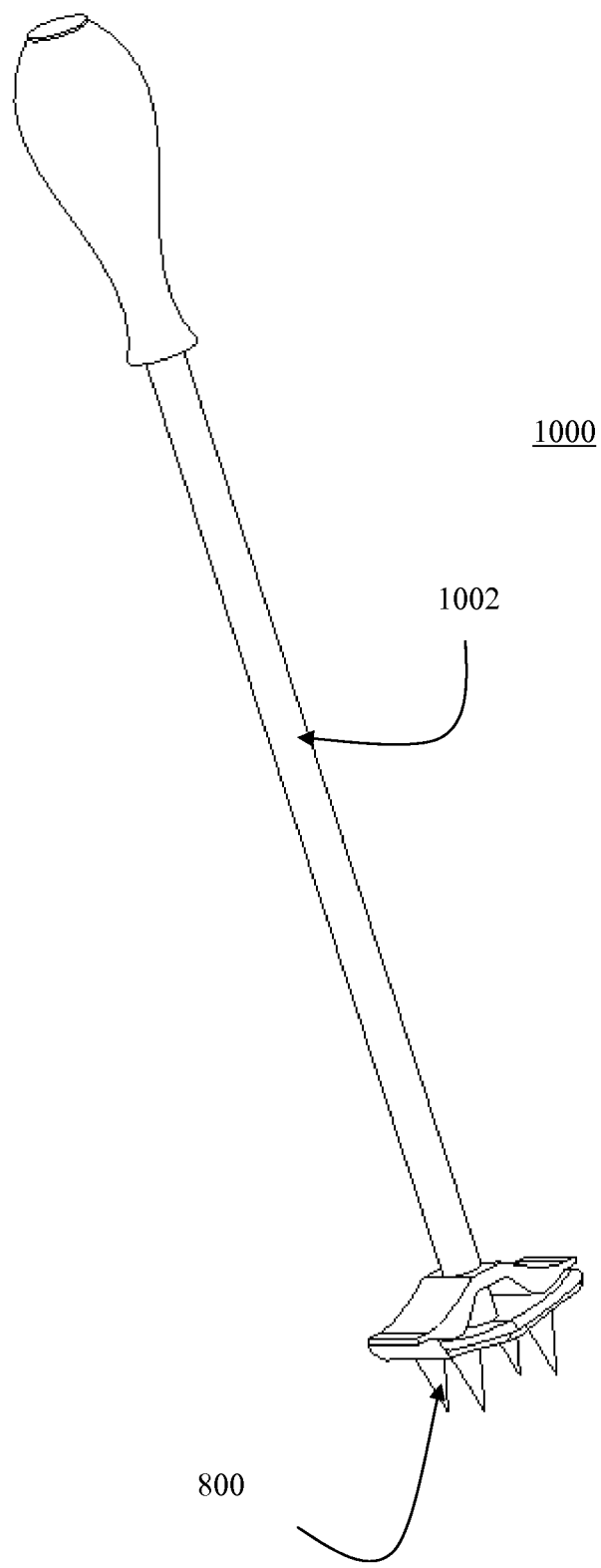

FIG. 10B illustrates the four pronged cervical facet staple impactor inserted into the cervical facet staple (Embodiment II).

Figure 10C:
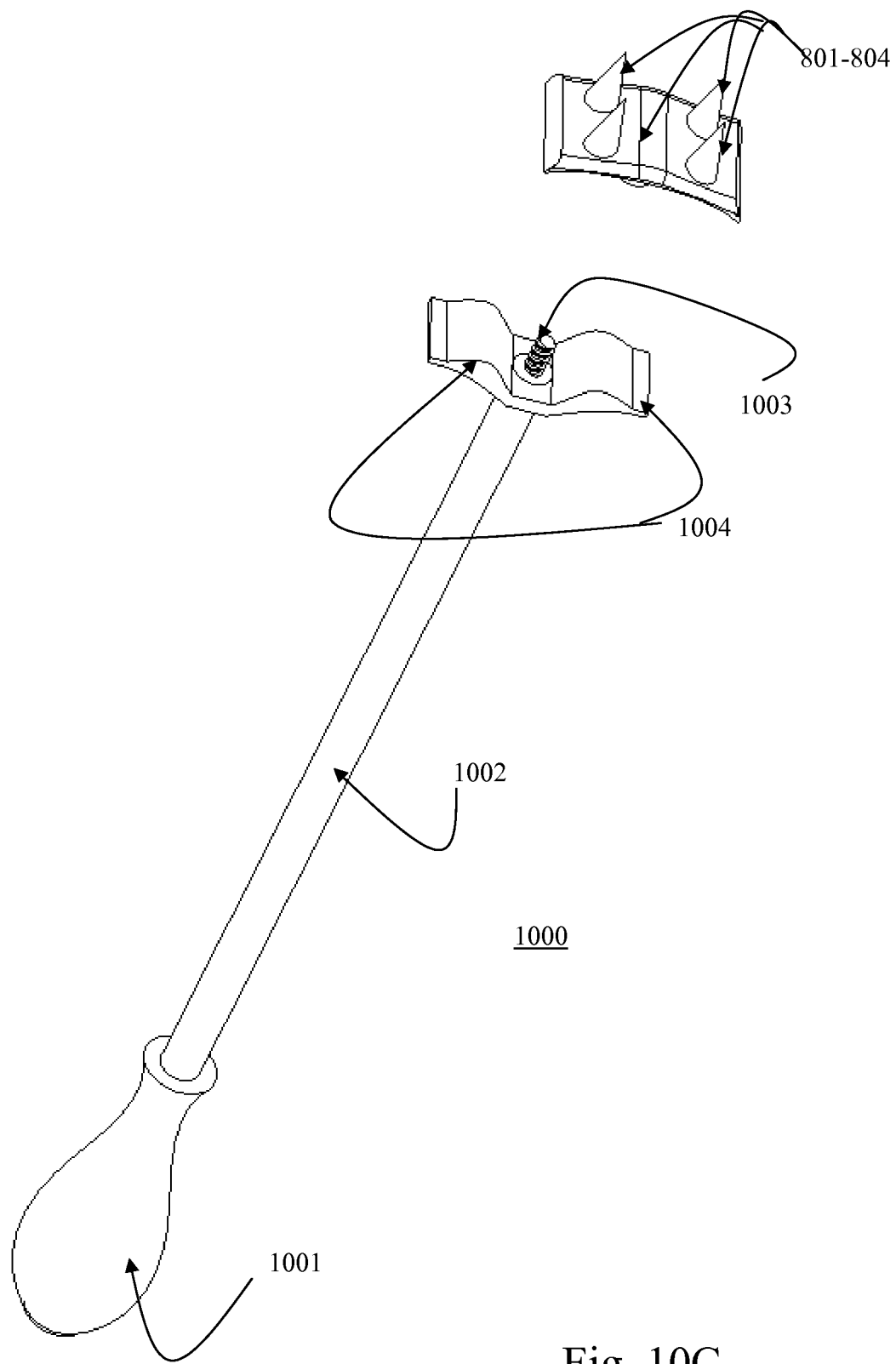

FIG. 10C illustrates an inferior-oblique perspective view of the four—pronged cervical facet staple impactor (Embodiment II).

Figure 11A:
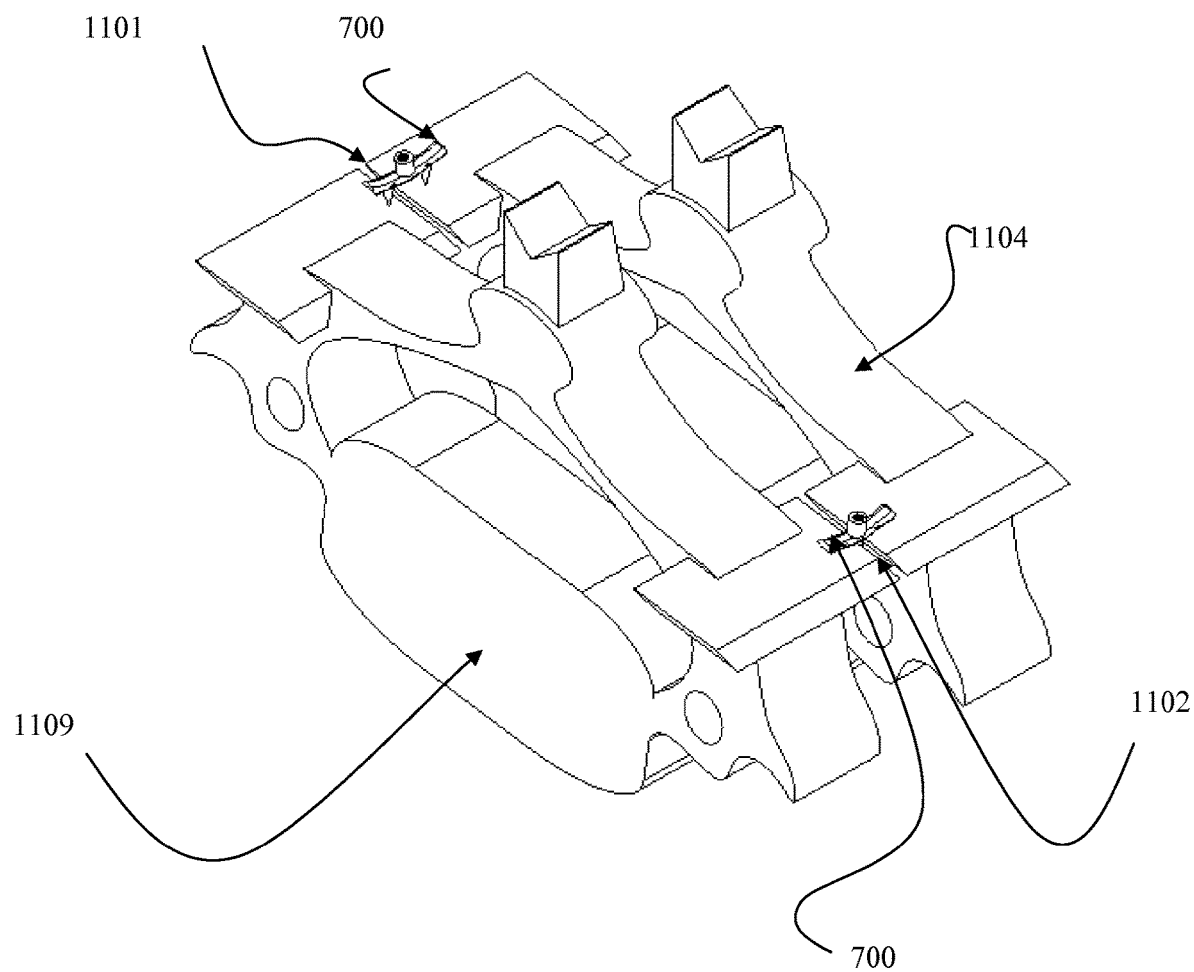

FIG. 11A illustrates placement of two-pronged cervical facet staples in a three-dimensional cervical spine.

Figure 11B:
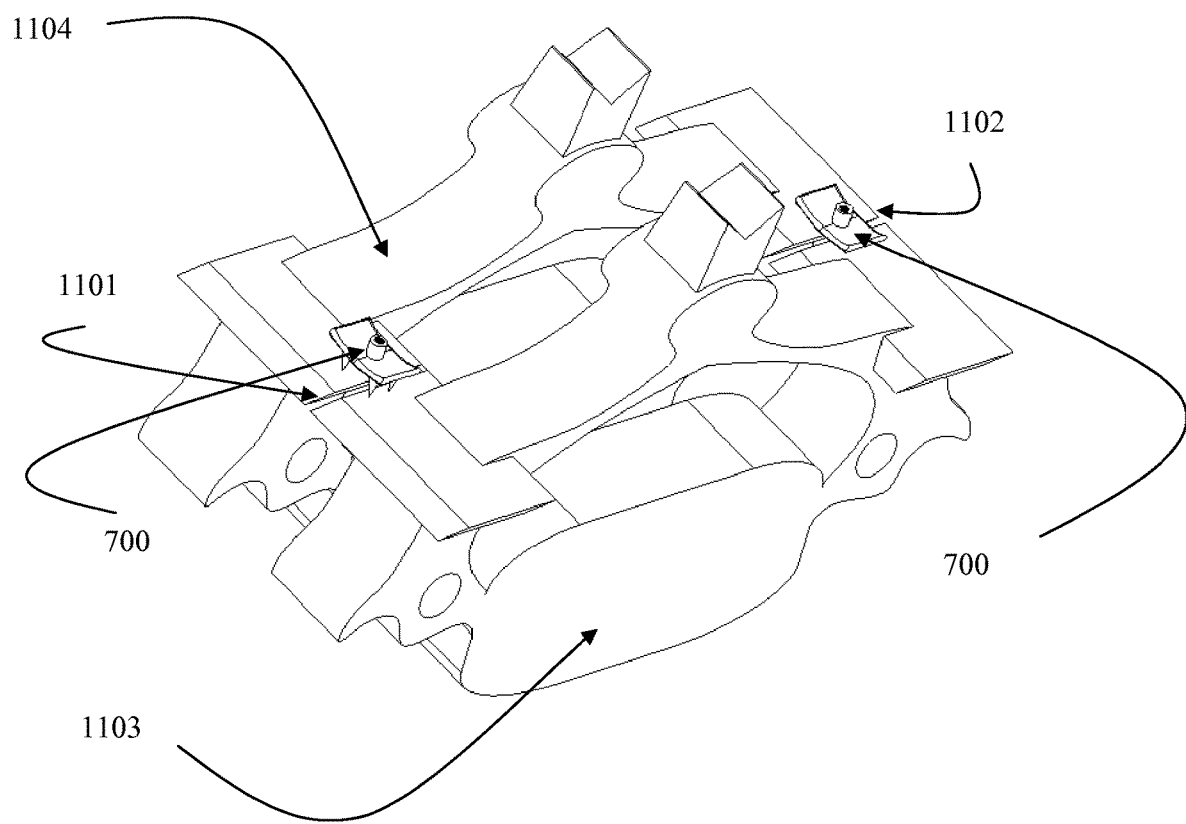

FIG. 11B illustrates placement of four-pronged cervical facet staples in a three-dimensional cervical spine.

Figure 11C:
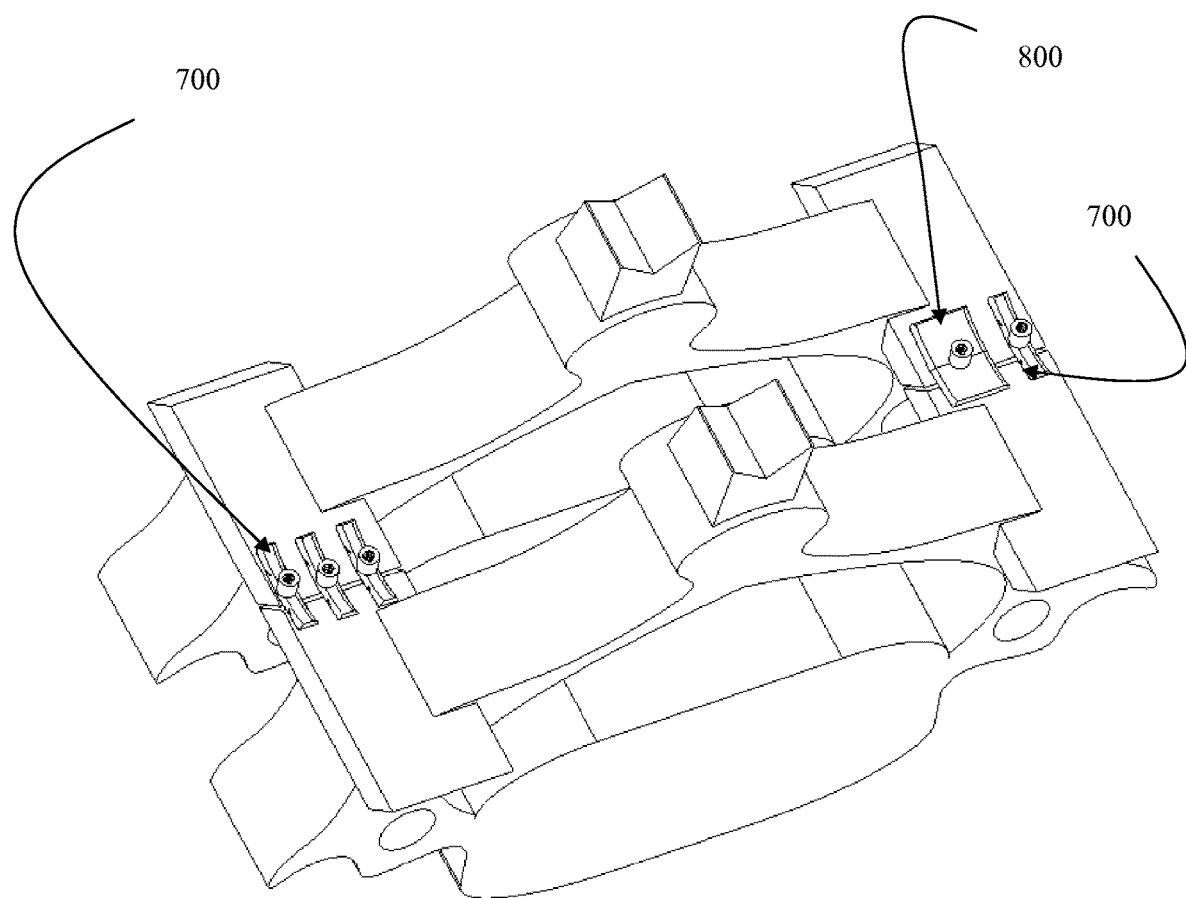

FIG. 11C illustrates modular placement of two and four pronged cervical facet staples in a three-dimensional cervical spine to achieve differing calibrated degrees of flexibility.

Figure 12A:
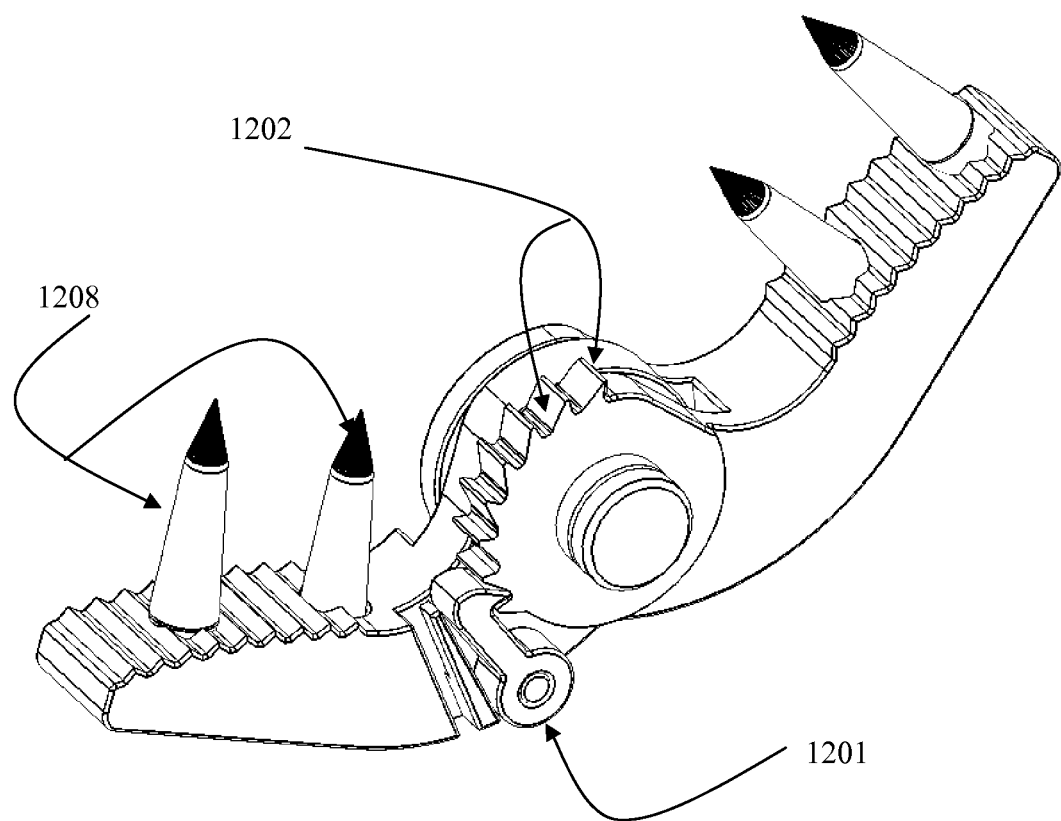
Figure 12B:
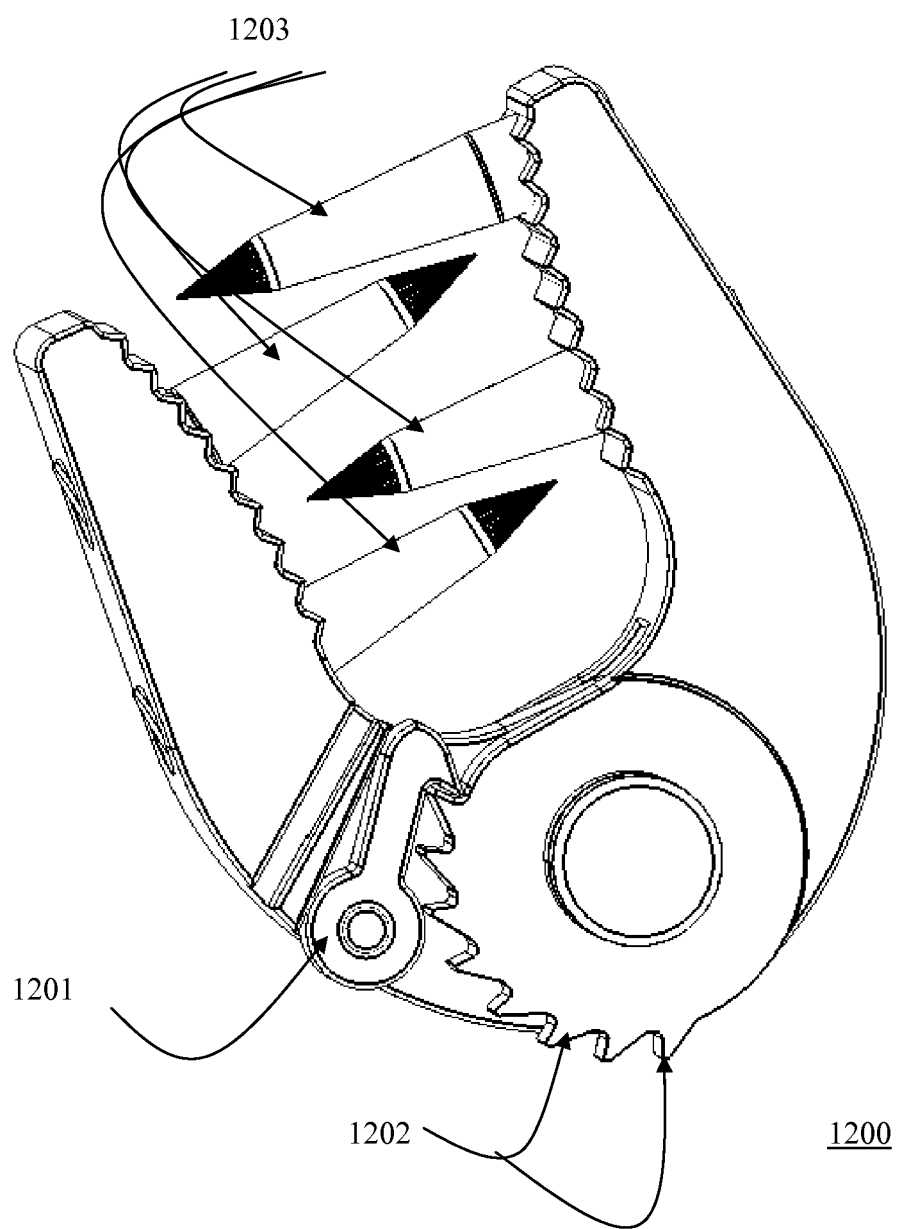

FIGS. 12 A-B illustrate the Lumbar facet joint staple with a calibrated ratcheting mechanism in opened (Figure A) and closed (Figure B) positions.

DETAILED DESCRIPTION OF THE INVENTION

1. The Medical Device

Referring to FIGS. 1-6, the above described problem can be solved in the thoracic and lumbar spine by insertion into the denuded intervertebral disc space multiple embodiments of screw box constructs with BDFT screws.

Figure 1A:
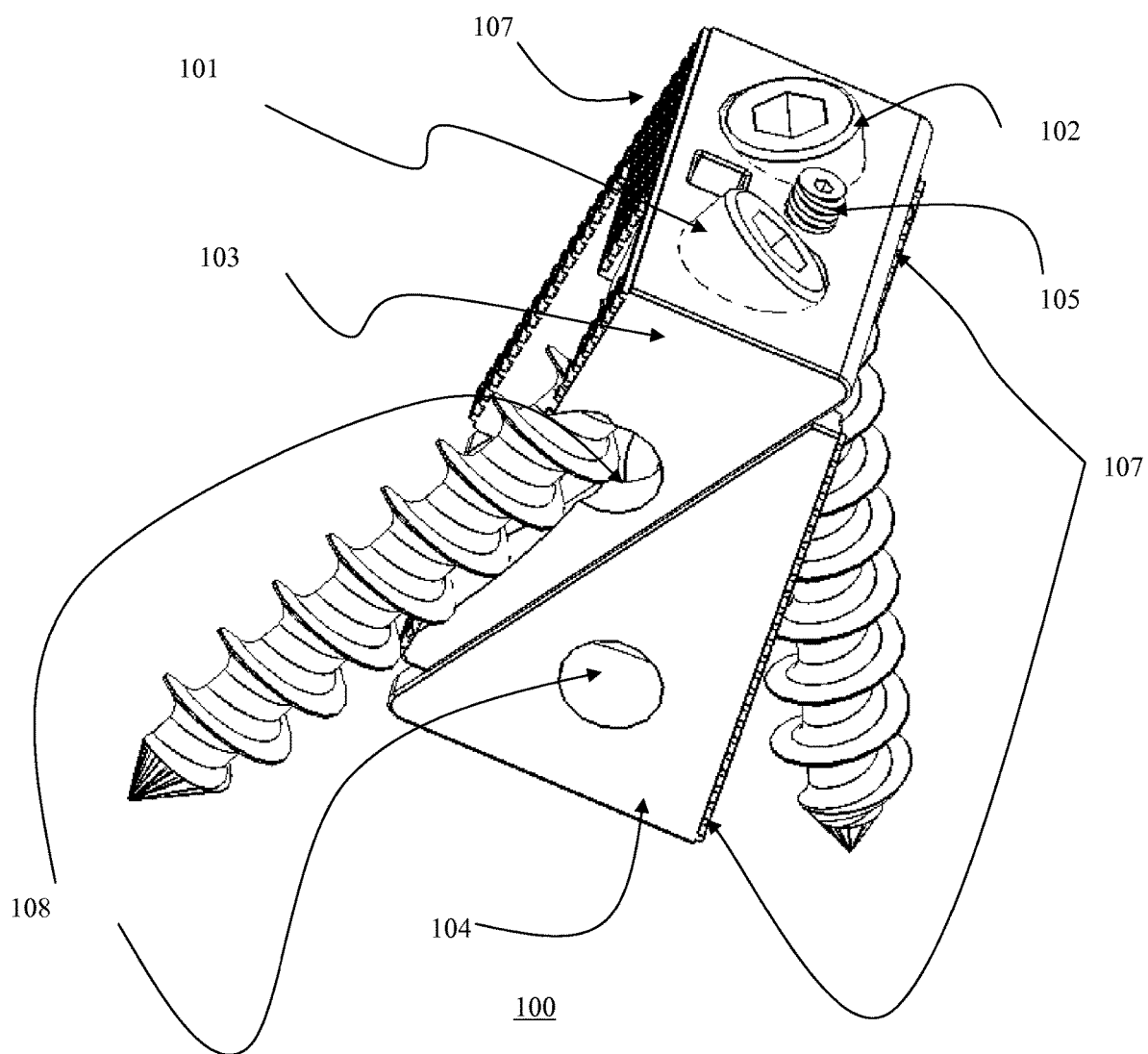
FIGS. 1A-D illustrate the Lumbar intervertebral screw box with one lateral oriented BDFT screw and one medially oriented two BDFT screw (Embodiment IA) in sagittal-oblique (FIG. 1A), superior perspective (FIG. 1B), inferior perspective (FIG. 1C) and exploded (FIG. 1D) views.
Figure 1B:
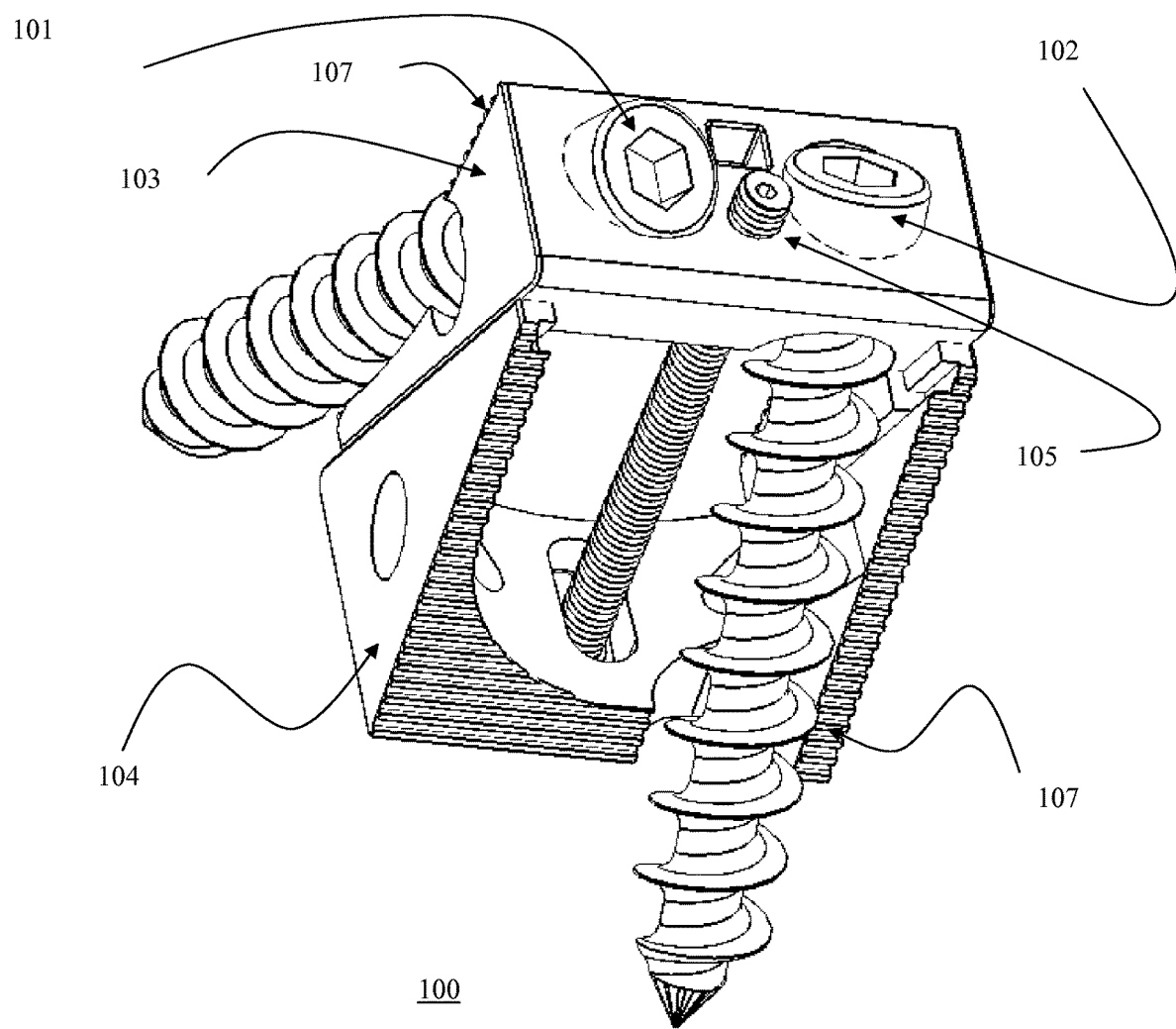
Figure 1C:
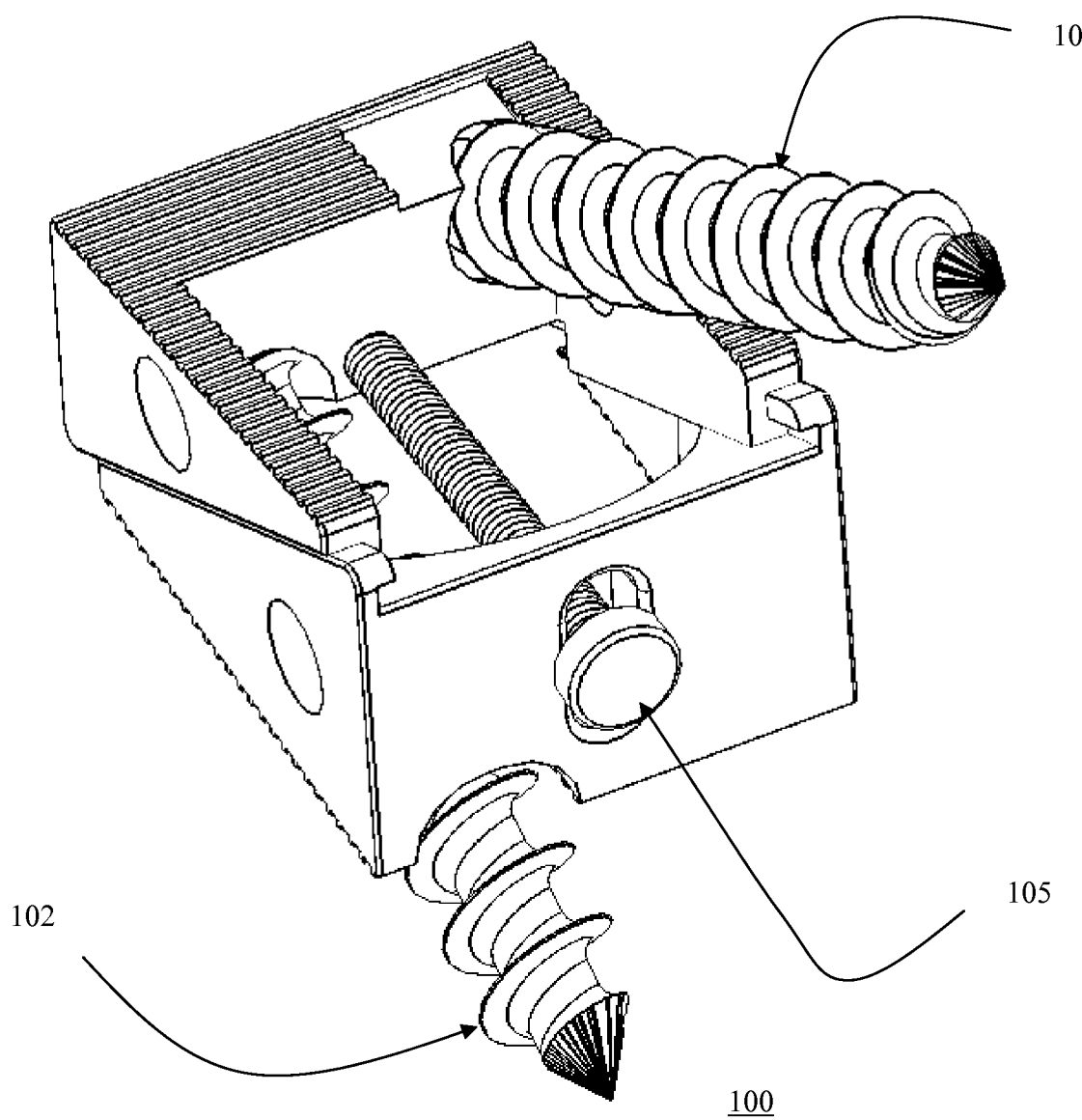
Figure 1D:
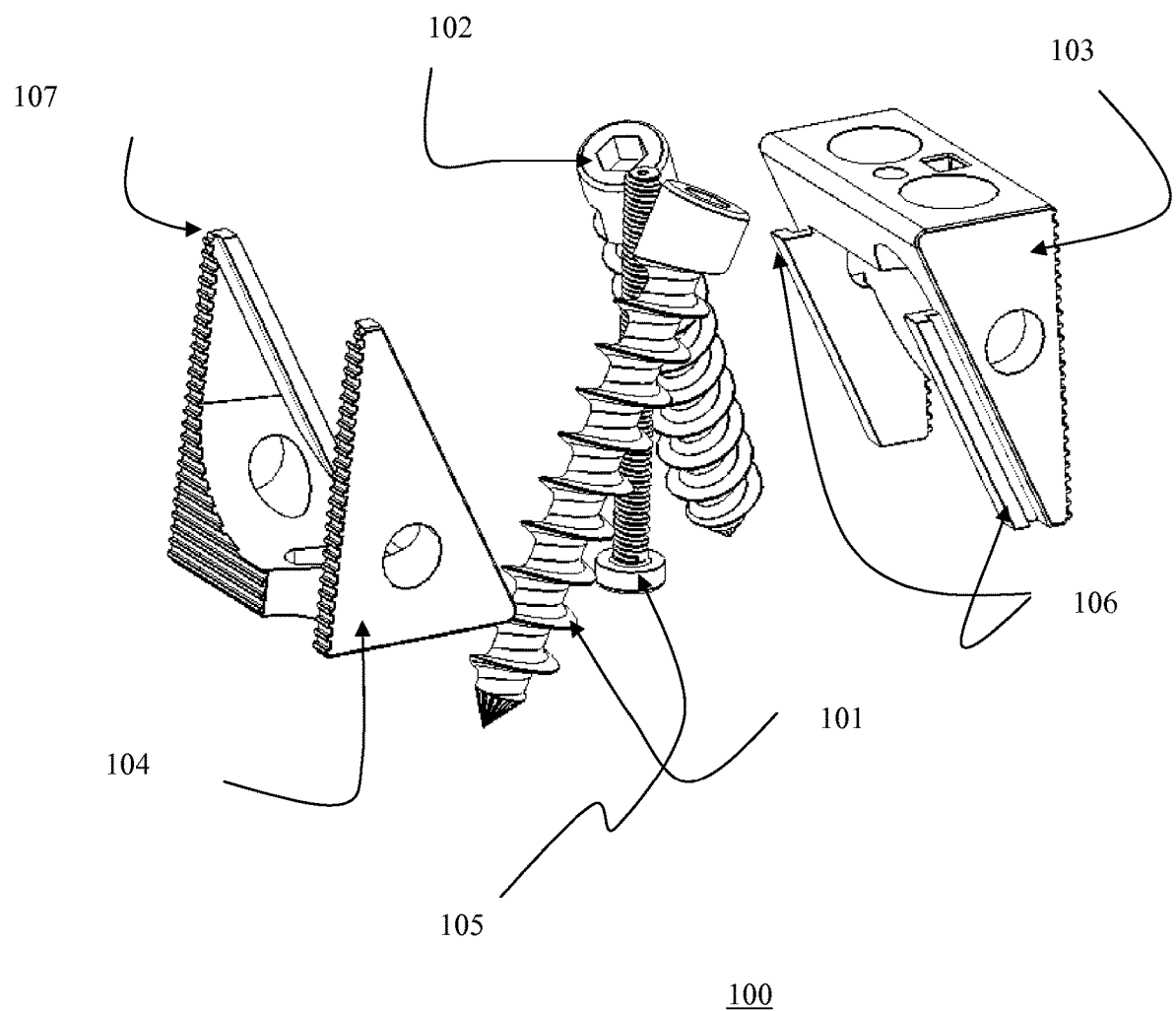
Figure 1E:
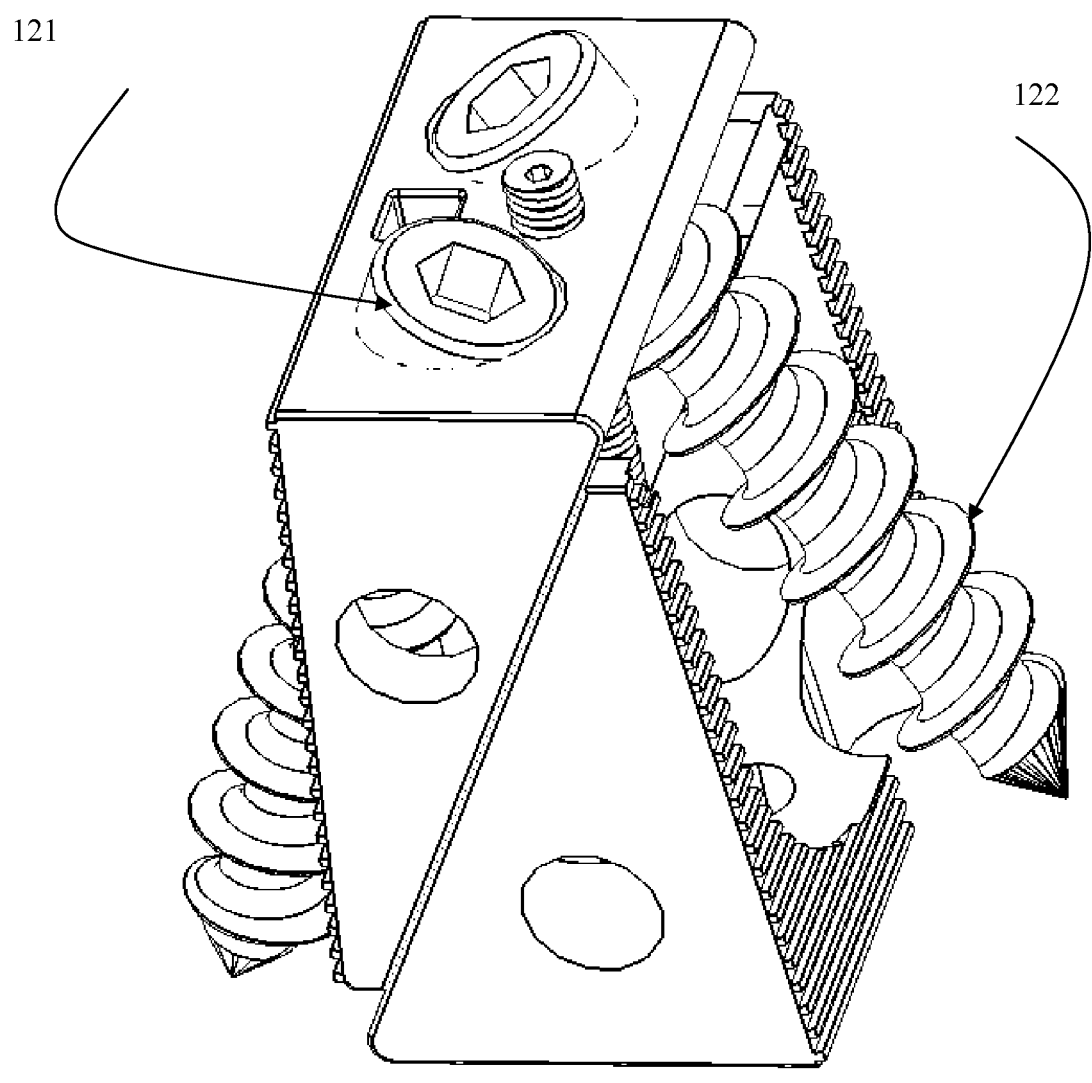
FIG. 1E illustrates the lumbar intervertebral expandable screw box with two lateral oriented BDFT screws (Embodiment IB; sagittal-oblique view).

FIGS. 1A-D illustrate three-dimensional views of the Lumbar intervertebral expandable screw box 100 with two BDFT screws 101, 102; one lateral and one medially oriented (Embodiment IA). FIG. 1E illustrates a sagittal-oblique view of the lumbar intervertebral expandable screw box 120 with two lateral oriented BDFT screws 121, 122 (Embodiment IB).

The expandable box 100 consists of top and bottom triangular sliding bases 103, 104 (FIG. 1-D). The superior and inferior segments of the height/depth adjusting screw 105 are integrated and connected to the two separate top and bottom triangular bases 103, 104, respectively. By turning this adjusting screw 105 back and forth i.e. clock-wise, and counter clockwise, the sliding rails 106 of the top triangular base 103 (FIG. 1D) slide up and down the rail inserts 107 on the bottom triangular base 104 (FIG. 1D). This action will simultaneously alter the intervertebral height and depth of the screw box 100 allowing individualized custom fitting of the screw box 100 conforming to the dimensions of the disc space.

Transvertebral screw 101 penetrates the top base 103, and transvertebral screw 102 traverses the bottom base 104 of the screw box 100. The two screws 101, 102 traverse the screw box 100 in opposing directions, bi-directionally (whether they are lateral or medially oriented). The external edges of the triangular bases 103, 104 in contact with vertebral body surfaces include ridges 107. This facilitates the screw box's 100 incorporation into and fusion with the superior and inferior vertebral bodies (FIGS. 1A-E). Both top and bottom screw box bases 103, 104 are perforated with holes 108 to allow bone placement for fusion. The entire construct, furthermore, is hollow to allow bone filling. Hence this device functions as both an intervertebral bone fusion spacer and bi-directional transvertebral screw fusion device.

Figure 2A:
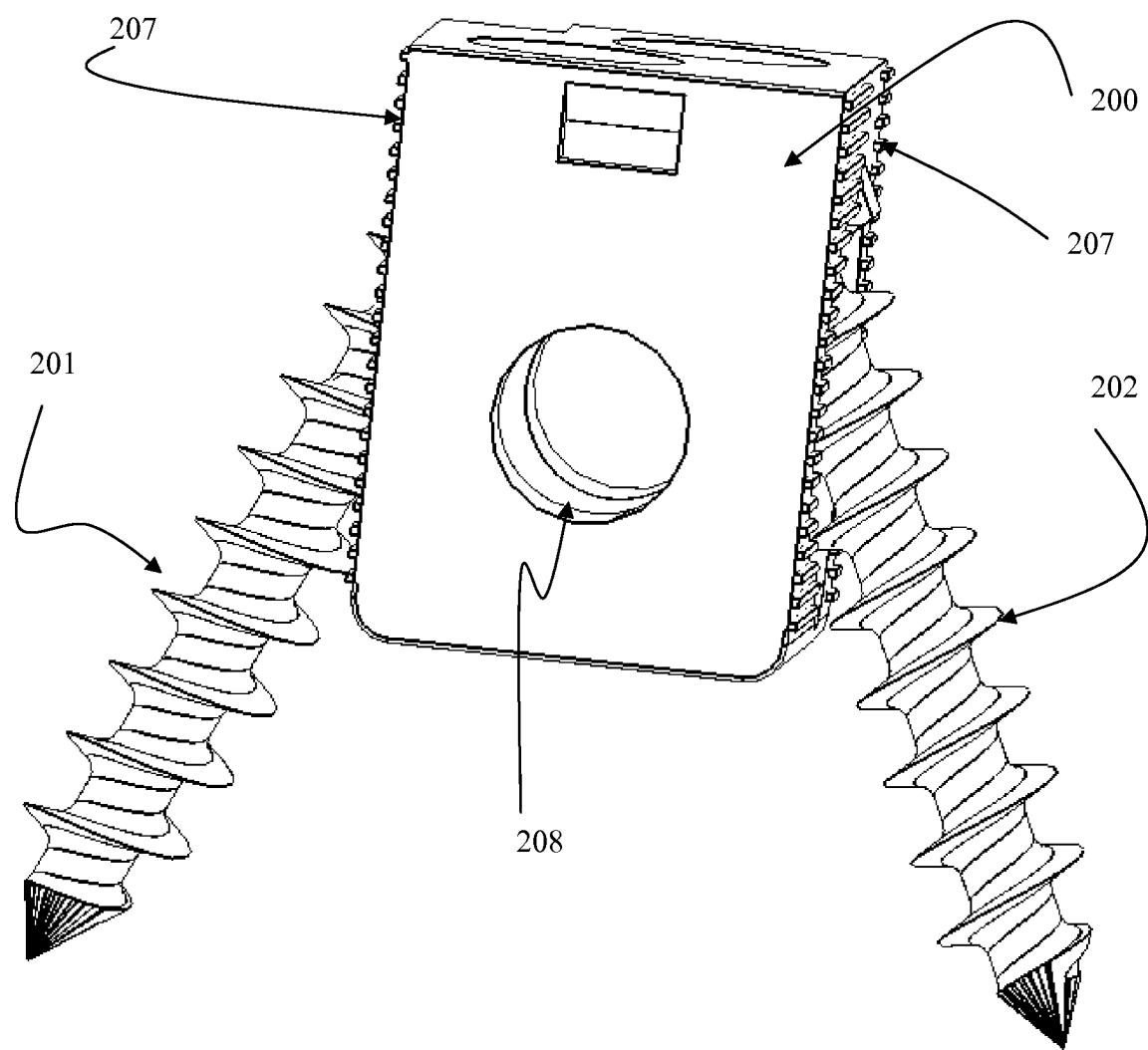
FIGS. 2A-C illustrate the Lumbar intervertebral non-expandable screw box with two BDFT screws (Embodiment II) in lateral (FIG. 2A), oblique (FIG. 2B), and superior perspective (FIG. 2C) views.
Figure 2B:
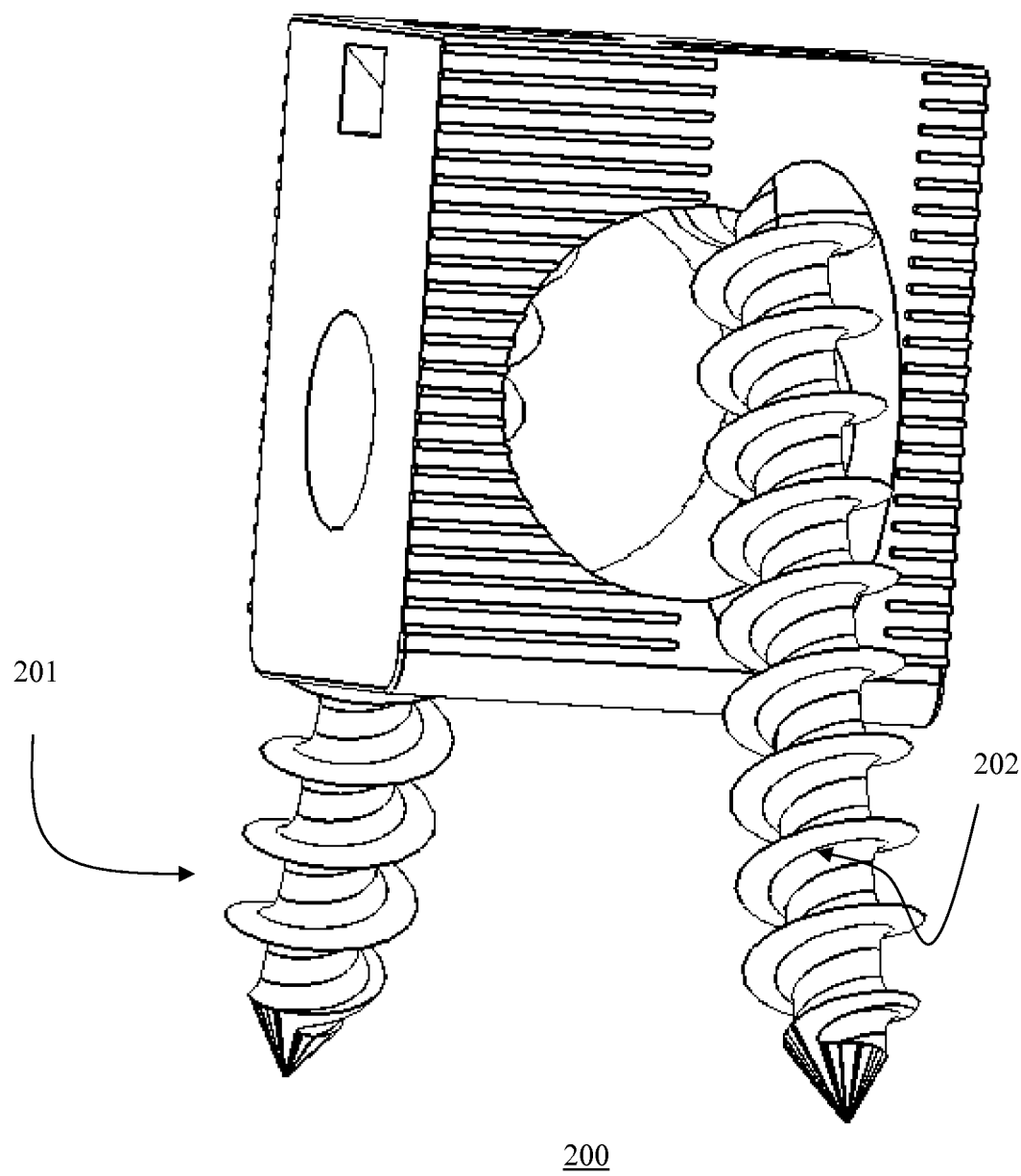
Figure 2C:
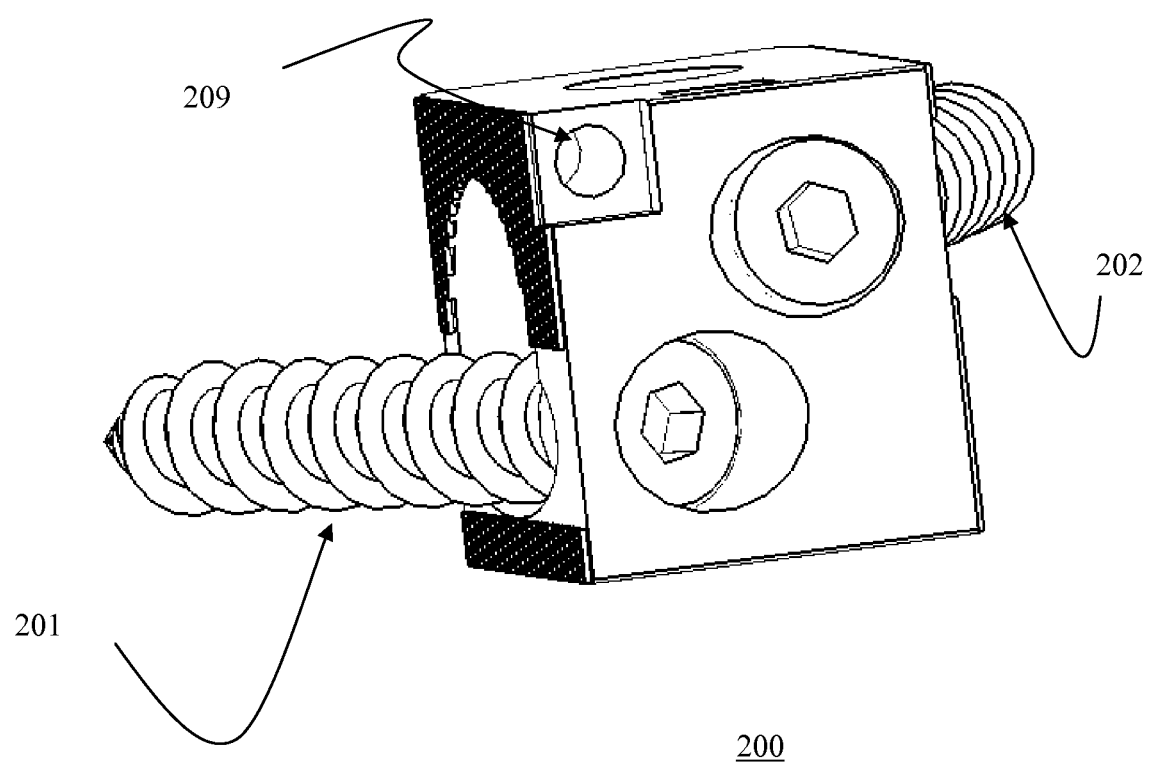

FIGS. 2A-C illustrate three-dimensional views of the Lumbar intervertebral non-expandable screw box 200 with two BDFT screws 201, 202 (Embodiment II). Screws 201 and 202 perforate and orient in opposing, superior and inferior directions. There are holes 208 and hollow spaces allowing packaging with bone. There are also holes which allow the traversal of screws. The superior and inferior edges include ridges 207 to facilitate integration and fusion with superior and inferior vertebral bodies. The expandable screw box 200 may include a screw insert 209 to attach a horizontal mini-plate (not shown). The self-contained internalized drill guides are at a 25 degree angle. The screw boxes can be designed with the internalized drill guides with different angles and/or different positions within the box.

Figure 3:
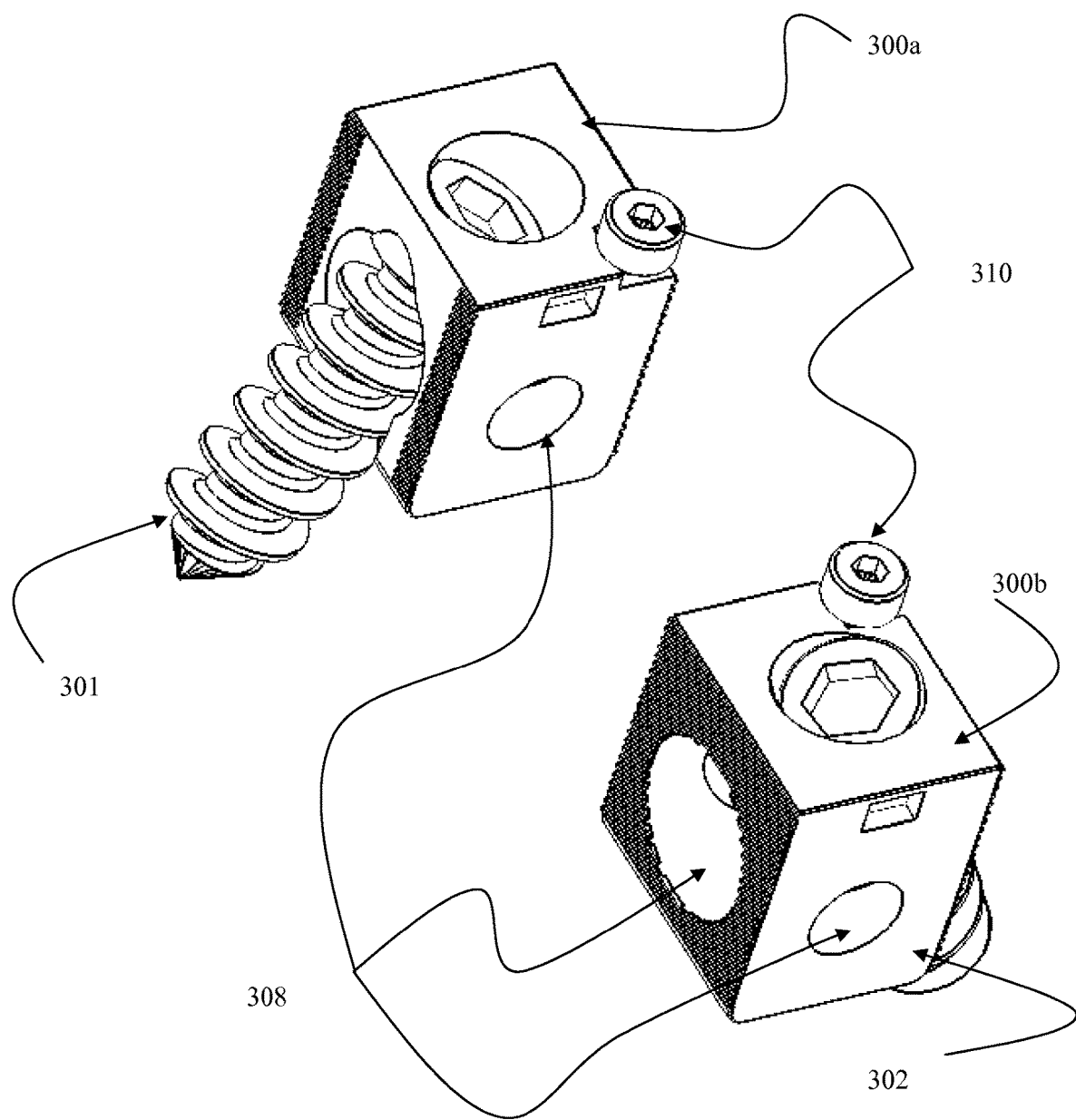
FIG. 3 illustrates a superior oblique perspective view of left and right lumbar intervertebral non-expandable screw boxes with one BDFT screw (Embodiment III).

FIG. 3 illustrates a three-dimensional view of left and right lumbar intervertebral non-expandable screw boxes 300a, 300b with one BDFT screw 301 or 302 (Embodiment III). It is roughly half the width of Embodiments I and II. Screw 301 is inserted into screw box 300a (left) and screw 302 is inserted into screw box 300b (right). There are holes 308 and hollow spaces allowing packing of bone to achieve biological fusion. The combined effect of one superior oriented and one inferior oriented screw fuses the superior and inferior vertebral bodies with small constructs. This also enables placement of larger dimension screws compared to embodiments I and II.

Figure 4A:
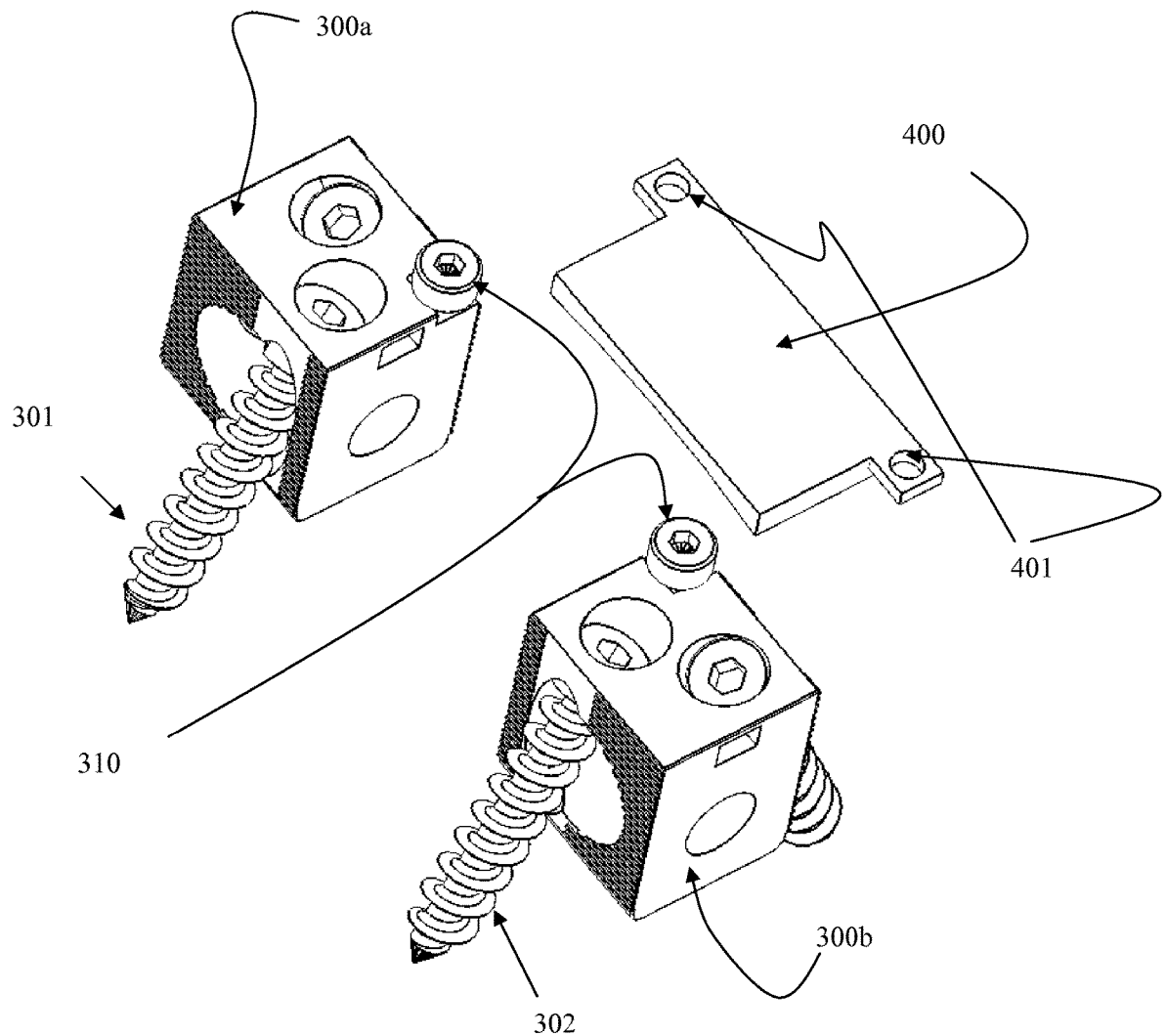
FIGS. 4A-B illustrate the horizontal intervertebral zero-profile mini-plate prior to insertion (FIG. 4A), and after insertion (FIG. 4B) into two non-expandable lumbar intervertebral screw boxes with two BDFT screws.
Figure 4B:
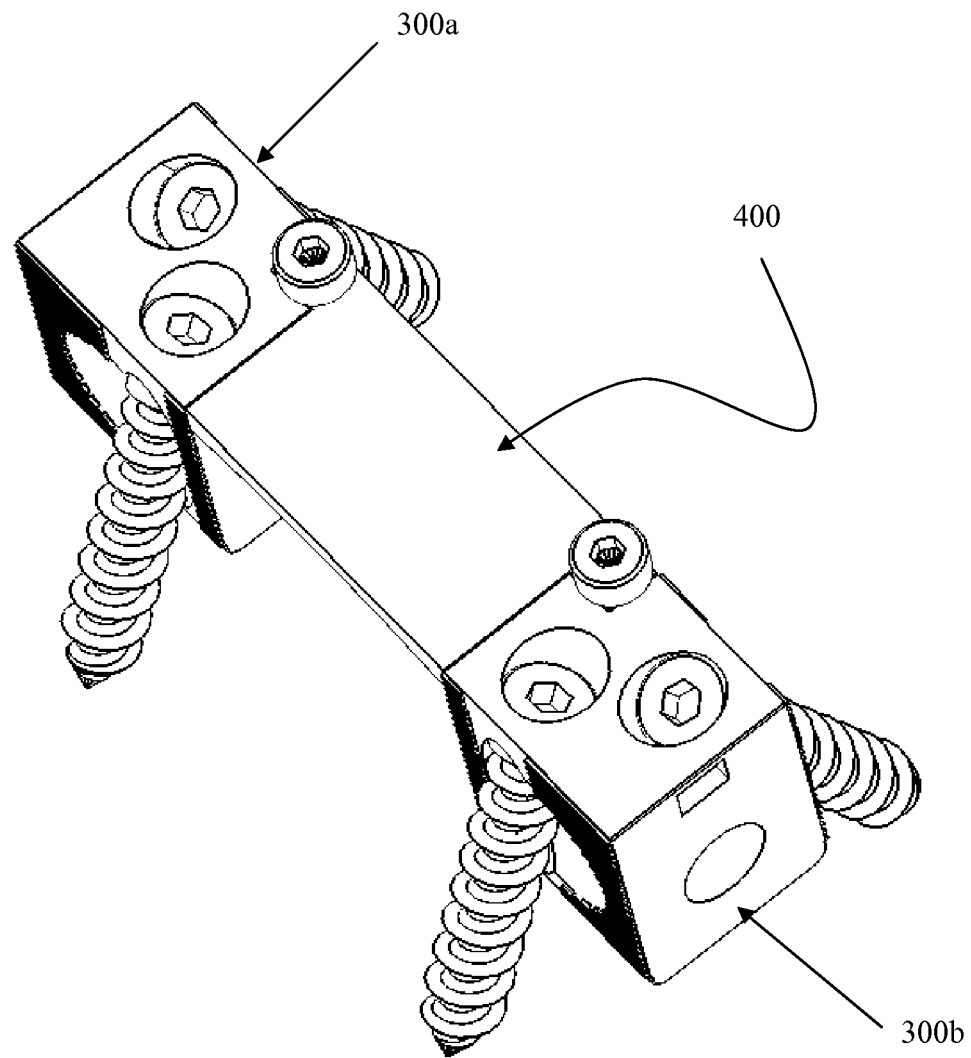

FIGS. 4A and B illustrate three-dimensional views of the horizontal intervertebral zero profile mini-plate 400 with two non-expandable lumbar intervertebral screw boxes 300a, 300b housing two BDFT screws 301, 302. FIG. 4A illustrates the perforations 401 within the plate 400 through which small plate securing screws 310 will be inserted to connect it to the built-in screw holes of the screw box 300a, 300b (FIG. 4B). The horizontal mini-plate 400 together with the top surfaces of left and right screw boxes 300a, 300b provide a physical barrier between the underlying bone placed beneath it (not illustrated), and the thecal sac and nerve roots above it (not illustrated).

Figure 4C:
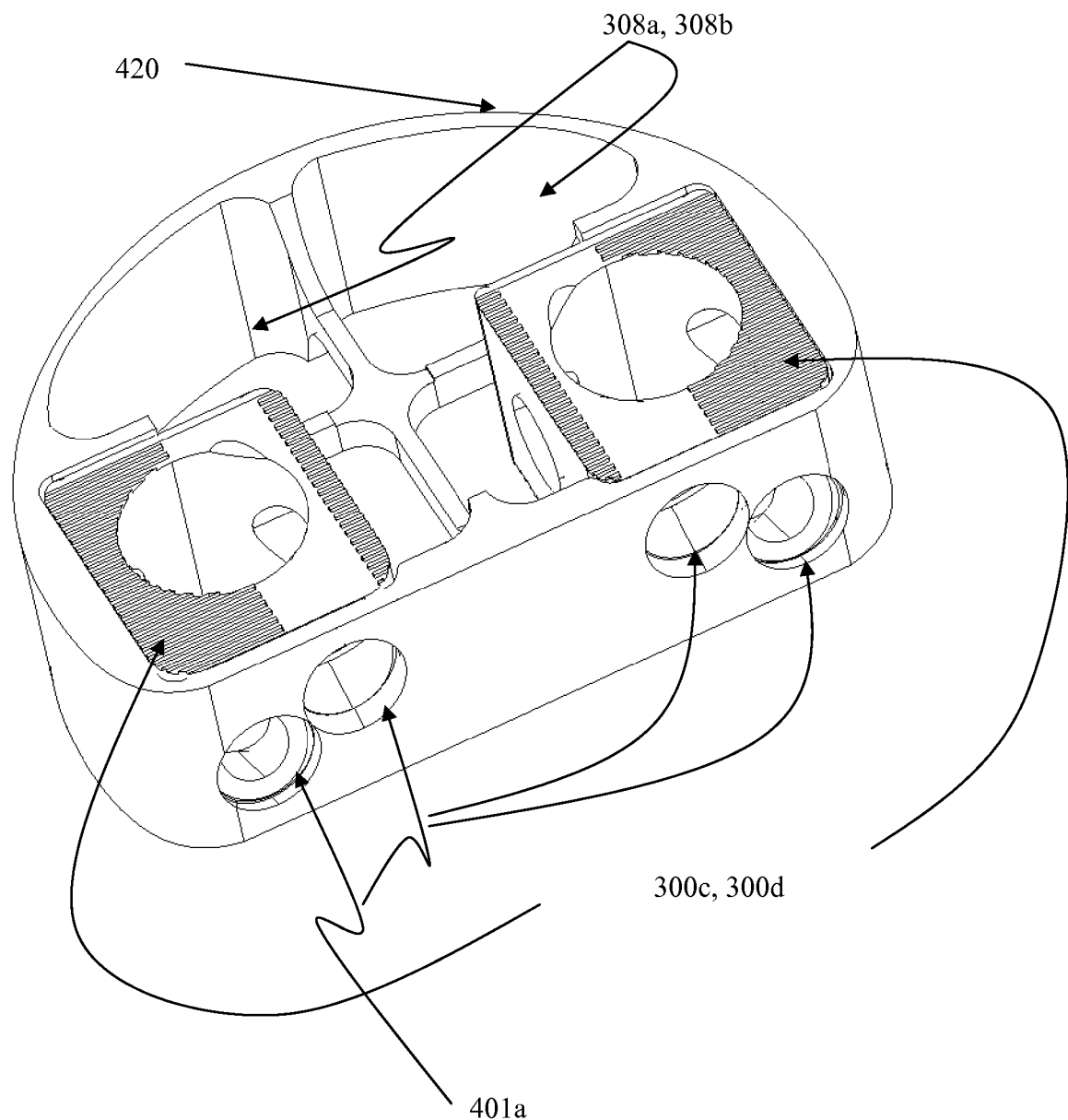
FIG. 4C illustrates two non-expandable lumbar intervertebral screw boxes with two screws within a large circumferential cage for anterior placement into the lumbar spine

FIG. 4C illustrates two screw boxes 300c, 300d within a circumferential cage 420 (2 in 1) construct which is designed for anterior placement into the lumbar spine. There are slots 308a, 308b for bone graft placement, both outside and inside the boxes. The circumferential cage 420 has perforations 401a for the placement of transvertebral screws (not shown).

FIGS. 5A-C illustrate three-dimensional views of the external drill/screw guide-box expander 500 which assists in screw trajectory and box expansion (embodiments IA-B). For embodiments II and III, the same instrument is utilized; however, an expanding Allen key component is not used.

The key components of this device include an Allen key 501, a spring 502, a handle 503, a griper 504 and a screw guide 505. The Allen key 501 when inserted in the insertion 514 and turned, turns the screw adjuster (FIG. 5C) which in turn regulates top and bottom triangular screw box base sliding, and hence box 200 width and depth. The griper 504 has griper prongs 506 which insert into grooves of the screw guide 505 and the screw box 200 (FIGS. 5A-D) thus perfectly aligning them.

FIG. 5D illustrates a superior oblique view of the screw guide 505 demonstrating insertions 509 for griper prong 506, built-in trajectory guides 511, 512 for insertions of screws 101 and 102, and the Allen key 501.

FIGS. 5E-G illustrate three-dimensional views of the sequential steps necessary for the external guide assembly. FIG. 5E illustrates the insertion of the Allen key 501 into the handle 503. FIG. 5F illustrates the insertion of the handle 503 through the spring 502 and griper 504. FIG. 5G illustrates insertion of the griper 504 into the screw guide 505.

FIGS. 5H-I illustrate three-dimensional views of a positioning tool 500a for impaction and placement of two transvertebral screws 201, 202 in the non-expandable screw box 200. The driver assembly 550 consists of a screw driver 551, a flexible shaft 552 and a square recess bit 553. This facilitates turning the screws 201, 202 into the bone. The flexible shaft 552 facilitates the avoidance of spinous processes which might hinder the screw driving if the shaft 552 were straight. The positioning tool 500a can have a rectangular handle, Embodiment I (FIG. 5H), or a circular handle, Embodiment II (FIG. 5I). This serves to position the screw box within the intervertebral space, and screws 201, 202 within the screw box. Once positioned, the screw box can be impacted by tapping the handle with a mallet (not shown). The positioning tool's 500a griper handle inserts into the screw guide and the box, which maintains alignment.

FIG. 6A illustrates a three-dimensional view of insertion of the construct (Embodiment I) into the lumbar intervertebral disc space.

FIG. 6B illustrates a three dimensional lateral view of insertion of the construct (Embodiment I) into the disc space with short screws. Placement with longer screws would capture more bone.

FIGS. 7A and B illustrate three-dimensional views of the two-pronged cervical facet staple 700 (Embodiment I). There is a staple base 701 which is contoured to align with the curved surface of the cervical facet joints. There is a superior impactor threaded insert 702. An impactor can be screwed into this insert 702 and then impacted with a mallet. The two spikes 703, 704 perforate the inferior and superior facets of the superior and inferior vertebral bodies hence leading to cervical facet joint fusion. The spikes can be designed with ridges and/or fishhooks to facilitate irreversible extraction.

FIGS. 8A-C illustrate three-dimensional views of the four-pronged cervical facet staple 800 (Embodiment II). Likewise it has a staple base 805 contoured specifically for the surface of the facet joint. It also has an impactor insert 806. The insertion of a device with four prongs 801-804 instead of two prongs further limits the degrees of motion of the joint hence making the fusion more rigid.

FIGS. 9 A-B illustrate a three-dimensional view of the two-pronged cervical staple impactor 900. It has a handle 901, a stem 902, and a screw insert 903 which can be screwed into the threaded staple insert. The impactor has two wings 904 which keep the staple base edges in place facilitating staple impaction. The handle 901 of the impactor 900 is broad in order to allow impaction by a mallet.

FIGS. 10A-C illustrate three-dimensional views of the four-pronged cervical staple impactor 1000 (Embodiment II). It has the same features as the two-pronged impactor 900, except its wings 1004 are broader accommodating the broader staple base. The impactor 1000 also includes a handle 1001, a stem 1002, and an impact screw 1003.

FIG. 11A illustrates a three-dimensional view of placement of the two pronged cervical facet staple 700 into a cervical spine model having vertebral body 1103 and lamina 1104. One staple 700 is perched on the joint 1101 prior to impaction. The other staple 700 is impacted.

FIG. 11B illustrates a three-dimensional view of placement of the four pronged cervical facet staple 800 into a cervical spine pre and post impaction.

FIG. 11C illustrates the concept of modularity and incremental diminution of movement of the joint by the modular placement of different combinations and permutations of varying numbers of two and four pronged cervical facet staples 700, 800. If one wishes to have the most flexible (least rigid) fusion, one would place a unilateral two pronged staple 700. One can increase i.e. calibrate increasing degrees of rigidity by increasing the number of prongs penetrating the facet joints bilaterally. In FIG. 11C each facet joint is fused using a total number of six prongs. One side this is accomplished by using three two pronged staples 700, and on the other side using one four pronged staple 800 and one two pronged staple 700. These two embodiments can be mixed and matched unilaterally or bilaterally to vary the degree of rigidity and conversely flexibility of fusion. The most flexible fusion at one level would be accomplished by one staple 700 (2 prongs). The highest level of rigidity would be achieved by placing two four pronged staples 800 on both sides totaling sixteen prongs. Intermediate degrees of relative joint motion can be modulated by insertion into the cervical facet joints staples in two-four prong increments from 2-16. Each additional prong further limits the degree of facet joint motion hence increasing rigidity, and conversely decreasing flexibility. Thus the novel modular use of these embodiments heralds an era of flexible cervical spine fusion.

FIGS. 12 A-B illustrate a lumbar facet joint staple 1200 in open and closed positions and having staple prongs 1203. This lumbar facet staple has been thoroughly described in our previous co-pending patent applications, Ser. No. 11/536,815, filed on Sep. 29, 2006, and Ser. No. 11/208,644, filed on Aug. 23, 2005, the relevant portion of each of which is hereby incorporated by reference hereinafter. The new improvement of this device includes a ratchet 1201. The staple 1200 can be incrementally closed with increased ratcheting over increasing number of spurs 1202. This achieves increasing calibrated levels of lumbar facet joint fusion, and conversely diminishing joint flexibility. This new designs further enhances the capacity to achieve flexible fusions in the lumbar spine.

2. The Surgical Method

Exemplary surgical steps for practicing one or more of the foregoing embodiments will now be described.

The posterior lumbar spine implantation of all the screw box 100, 200, 300 embodiments, with BDFT screws, and horizontal mini-plate 400 can be implanted via previously described posterior lumbar interbody fusion (PLIF) or posterior transforaminal lumbar interbody fusion (TLIF) procedures. The procedures can be performed open, microscopic, closed tubular or endoscopic. Fluoroscopic guidance can be used with any of these procedures.

After adequate induction of anesthesia, the patient is placed in the prone position. A midline incision is made for a PLIF procedure, and one or two parallel paramedian incisions or a midline incision is made for the TLIF procedure. For the PLIF, a unilateral or bilateral facet sparing hemi-laminotomy is created to introduce screw box 100, 200, 300 embodiments I-III into the disc space, after it is adequately prepared.

For the TLIF procedure, after unilateral or bilateral dissection and drilling of the inferior articulating surface and the medial superior articulating facet the far lateral disc space is entered and a circumferential discectomy is performed. The disc space is prepared and the endplates exposed.

Then one screw box 100, 200, 300 of either embodiments I-III is placed on either right, left or both sides. Then another screw box of embodiments 100, 200, 300 I-III is placed on the contralateral side. For embodiment I the external screw guide 505/box expander is attached to the screw box (FIGS. 5A-H). First the Allen key 501 is screwed until the box conforms perfectly to the height and depth of the space. Then a pilot hole can be drilled or an awl can start a pilot hole in the vertebral bodies. Then a transvertebral screw is screwed into the vertebral body via the built-in box screw guides 505. For difficult angles, an angled screw driver can be employed.

For embodiments II-III the same method is used for placing screws, except the Allen key 501 is not utilized in the absence of plate expansion.

If bilateral constructs have been inserted, bone is packed into the intervertebral space, as well as within the device. Then the horizontal intervertebral zero profile mini-plate 400 is slid beneath the thecal sac and is secured to both left and right screw boxes with small mini-plate screws 210 (FIGS. 4A-B). This prevents bone intrusion into the thecal sac and hence possible nerve root compression.

FIGS. 6A and B illustrate the process of insertion and final placement of the construct into the lumbar spine. The mini-plates 400 can come in different horizontal lengths and widths to accommodate different intra and inter-patient disc space diameters. The BDFT screws can come in different widths, lengths and thread designs.

The anterior thoracic and lumbar spine implantation of one, two or three screw box constructs 100, 200, 300 and BDFT screws can be performed in a similar manner to the posterior application. Likewise, a horizontal mini-plate 400 can be used to cap two or three screw box constructs 100, 200, 300 (one placed midline deeply, one placed left and one placed right, forming a triangulation). Alternatively two screw box constructs may be placed into a circumferential ring for anterior placement. Anterior placement of these devices can be performed into the L4/5 and L5/S1 spaces on the supine anesthetized patient via previously described open microscopic or endoscopic techniques. Once the disc space is exposed and discectomy and space preparation are performed, placement of one, two or three screw box embodiments 100, 200, 300 (I-III) or a 2 in I construct can be placed. The screw placement is facilitated by the internal screw guides, and different positioning tools ((FIG. 5). A right angled screw driver and/or ratchet could alternatively be employed A capping mini-plate 400 may be applied if desirable. The mechanism of screw placement and mini-plate 400 attachment are identical to what was described above.

The posterior placement of screw box constructs 100, 200, 300 alone or combined with horizontal mini-plates 400 into the thoracic spine can be performed via previously described transpedicular approaches; open or endoscopic. The anterior placement into the thoracic spine can be accomplished via a trans-thoracic approach. Once the disc space is exposed via either approach, any combination of the above mention Embodiments (I-III) can be inserted. Engagement of the devices is identical to what was mentioned above.

For posterior placement of cervical facet staple 700, 800 embodiments, after adequate induction of anesthesia the patient is flipped prone and his head and neck secured. A single midline or two para-median incisions are made for unilateral or bilateral or multilevel placement of staples. Ultimately the facet joint is exposed. Alternatively and preferably this can be performed percutaneously under fluoroscopic guidance with intravenous sedation. The staple 700, 800 (Embodiments I or II) is loaded into the impactor 900, 1000. The staple 700, 800 is placed on the two articulating cervical facets, and then impacted into the joint. To achieve modular calibrated fusion different combinations and permutations of cervical facet stales can be inserted ranging from a single unilateral two pronged staple providing a high degree of flexibility to a total of four bilaterally placed four pronged staples 800 (16 prongs) leading to the highest degree of rigidity. Additional bone may or may not be placed in its vicinity to facilitate permanent and solid fusion. This procedure can be performed open, closed, percutaneously, tubulary, endoscopically or microscopically. FIGS. 11 A-C illustrates placement of the staples 700, 800 in the cervical spine.

We have previously described surgical placement of the lumbar facet joint staple in our two co-pending patents. The surgical procedure for this device is identical to that which has been previously mentioned.

The present inventions may provide effective and safe techniques that overcome the problems associated with current transpedicular based cervical, thoracic and lumbar fusion technology, and for many degenerative stable and unstable spine disease. These inventions could replace much pedicle screw-based instrumentation in many but not all degenerative spine conditions.

The speed and simplicity of placement of cervical and lumbar facet staples, and placement of Lumbar screw box— BDFT constructs far exceeds that of current pedicle screw technology. Furthermore, these devices have markedly significantly decreased risk of misguided screw placement, and hence decreased risk of neural and vascular injury, and blood loss. In the lumbar spine BDFT screw constructs and facet staples could be applied modularly in different combinations to achieve different degrees of rigidity (flexibility). Patients having these devices would have decreased recovery and back to work time. These devices most likely lead to similar if not equal fusion with significantly less morbidity, and hence overall make them a major advance in the evolution of spinal instrumented technology leading to advances in the care of the spinal patient.

Another major novelty and advance is the introduction of simple and safe modular calibrated cervical flexible fusion. To our knowledge neither a similar device nor a similar mathematical concept of modular joint flexibility/fusion calibration has been postulated for the cervical spine or for any other articulating joint.

To our knowledge there have not been any previously described similar posterior lumbar and thoracic combined spacer and screw constructs. These devices can similarly be modified to stabilize bone fractures throughout the entire body. To our knowledge the description of zero to subzero profile anterior or posterior horizontal spinal plates which traverse the diameter of the disc space has not been previously described.

We claim:
1. A bidirectional fixating intervertebral implant system, the system comprising:
an intervertebral cage comprising a top wall, a bottom wall, a first sidewall and a second sidewall, and wherein the intervertebral cage defines:
first and second disc-facing surfaces having first and second sets of ridges on opposing sides of the top wall, the first sidewall, and the second sidewall,
an open space between the top wall, the bottom wall, the first sidewall, and the second sidewall capable of receiving bone filling for biological bone fusion,
a first internal anchor guide having a first entry opening and a first exit opening, the first entry opening formed entirely a top surface of the top wall and the first exit opening formed partially in a bottom surface of the top wall, partially in the first disc-facing surface of the top wall, and partially in the first disc-facing surface of the first sidewall,
a second internal anchor guide having a second entry opening and a second exit opening, the second entry opening formed entirely the top surface of the top wall and the second exit opening formed partially in the bottom surface of the top wall, partially in the second disc-facing surface of the top wall and partially in the second disc-facing surface of the first sidewall, wherein the first internal anchor guide and the second internal anchor guide are angled to orient anchor members bi-directionally,
a top indentation extending into the top surface of the top portion,
a top hole extending into the top surface of the top portion at an angle that is substantially perpendicular to the top surface, wherein the top hole is positioned in the top indentation,
a first side hole extending through the first sidewall into the open space,
a second side hole extending through the second sidewall into the open space, wherein the second side hole is positioned substantially opposite of the first side hole,
a first side indentation positioned on the first sidewall between the first side hole and the top surface of the top wall, and
a second side indentation positioned on the second sidewall between the second side hole and the top surface of the top wall,
a first anchor having a first anchor head, a first anchor tip that is pointed, and a first anchor body extending between the first anchor head and the first anchor tip, wherein the first anchor body is sized and configured to be inserted through the first internal anchor guide at a first angle so the first anchor extends from the intervertebral cage into a first vertebral body adjacent the intervertebral cage when inserted in a disc space; and
a second anchor having a second anchor head, a second anchor tip that is pointed, and a second anchor body extending between the second anchor head and the second anchor tip, wherein the second anchor body is sized and configured to be inserted through the second internal anchor guide at a second angle different than the first angle so the second anchor extends from the intervertebral cage into a second vertebral body adjacent the intervertebral cage when inserted in the disc space.
2. The implant system of claim 1, wherein the first and second anchors are first and second screws.
3. The implant system of claim 1, wherein the top wall of the intervertebral cage has a thickness that is greater than a thickness of each of the sidewalls.
4. The implant system of claim 1, wherein the first internal anchor guide and the second internal anchor guide are symmetrically disposed on each side of a center point of the intervertebral cage along a longitudinal axis of the top wall of the intervertebral cage.
5. The implant system of claim 1, wherein the open space extends from an inner surface of the first sidewall to an inner surface of the second sidewall.
6. The implant system of claim 1, wherein the open space extends from an inner surface of the first sidewall to an inner surface of the second sidewall and extends from an inner surface of the top wall to an inner surface of the bottom wall.
7. The implant system of claim 1, wherein the intervertebral cage is sized and configured to be inserted posteriorly in a lateral aspect of a posterior lumbar spine.
8. The implant system of claim 7, wherein the intervertebral cage is a first intervertebral cage, wherein the implant system comprises a second intervertebral cage defining substantially the same features as those of the first intervertebral cage, and wherein the second intervertebral cage is sized and configured to be inserted posteriorly in the lumbar spine along with the first intervertebral cage.
9. The implant system of claim 1, wherein the top hole is a threaded circular hole.
10. The implant system of claim 1, and further comprising means for inserting the intervertebral cage and guiding trajectory of the first and second anchors.
11. The implant system of claim 1, and further comprising an insertion tool having a proximal end and a distal end, wherein the insertion tool defines first and second tool anchor guides at the distal end, wherein the distal end of the insertion tool is configured to engage the intervertebral cage with the first and second tool anchor guides aligned with the first and second internal anchor guides of the intervertebral cage.
12. The implant system of claim 11, wherein the insertion tool has first and second projections extending from the distal end and positioned to engage the first and second sidewalls of the intervertebral cage.
13. The implant system of claim 1, wherein the top surface of the top wall is flat except for the first and second internal anchor guides, the top indentation, and the top hole.
14. A method of operating the implant system of claim 1, the method comprising:
preparing a disc space in a lateral aspect of a lumbar spine to receive the intervertebral cage;
inserting the intervertebral cage posteriorly into the lateral aspect of the disc space of the lumbar spine;
after the intervertebral cage is positioned in the lateral aspect of the disc space, inserting the first anchor posteriorly through the first internal anchor guide and into the first vertebral body to secure the intervertebral cage with respect to the first vertebral body; and
after the intervertebral cage is positioned in the lateral aspect of the disc space, inserting the second anchor posteriorly through the second internal anchor guide and into the second vertebral body to secure the intervertebral cage with respect to the second vertebral body.
15. The method of claim 14, wherein the intervertebral cage is inserted via an insertion tool having a proximal end and a distal end, wherein the insertion tool defines first and second tool anchor guides at the distal end, wherein the distal end of the insertion tool is configured to engage the intervertebral cage with the first and second tool anchor guides aligned with the first and second internal anchor guides of the intervertebral cage, and wherein the first and second anchors are inserted through the first and second tool anchor guides, respectively, into the first and second internal anchor guides, respectively, while the insertion tool is engaged with the intervertebral cage.

16. A bidirectional fixating intervertebral implant system, the system comprising:

an intervertebral cage sized and configured to be inserted posteriorly in a lateral aspect of a posterior lumbar spine and comprising a top wall, a bottom wall, a first sidewall and a second sidewall, wherein the top wall of the intervertebral cage has a thickness that is greater than a thickness of each of the sidewalls, and wherein the intervertebral cage defines:

first and second disc-facing surfaces having first and second sets of ridges on opposing sides of the top wall, the first sidewall, and the second sidewall, an open space between the top wall, the bottom wall, the first sidewall, and the second sidewall capable of receiving bone filling for biological bone fusion, a first internal anchor guide having a first entry opening and a first exit opening, the first entry opening formed entirely a top surface of the top wall and the first exit opening formed partially in a bottom surface of the top wall, partially in the first disc-facing surface of the top wall, and partially in the first disc-facing surface of the first sidewall, a second internal anchor guide having a second entry opening and a second exit opening, the second entry opening formed entirely the top surface of the top wall and the second exit opening formed partially in the bottom surface of the top wall, partially in the second disc-facing surface of the top wall and partially in the second disc-facing surface of the first sidewall, wherein the first internal anchor guide and the second internal anchor guide are angled to orient anchor members bi-directionally, a top indentation extending into the top surface of the top portion, a circular top hole extending into the top surface of the top portion at an angle that is substantially perpendicular to the top surface, wherein the circular top hole is positioned in the top indentation, and wherein the top surface of the top wall is flat except for the first and second internal anchor guides, the top indentation, and the circular top hole, a first side hole extending through the first sidewall into the open space, a second side hole extending through the second sidewall into the open space, wherein the second side hole is positioned substantially opposite of the first side hole, a first side indentation positioned on the first sidewall between the first side hole and the top surface of the top wall, and a second side indentation positioned on the second sidewall between the second side hole and the top surface of the top wall, a first anchor having a first anchor head, a first anchor tip that is pointed, and a first anchor body extending between the first anchor head and the first anchor tip, wherein the first anchor body is sized and configured to be inserted through the first internal anchor guide at a first angle so the first anchor extends from the intervertebral cage into a first vertebral body adjacent the intervertebral cage when inserted in a disc space;

a second anchor having a second anchor head, a second anchor tip that is pointed, and a second anchor body extending between the second anchor head and the second anchor tip, wherein the second anchor body is sized and configured to be inserted through the second internal anchor guide at a second angle different than the first angle so the second anchor extends from the intervertebral cage into a second vertebral body adjacent the intervertebral cage when inserted in the disc space; and an insertion tool having a proximal end and a distal end, wherein the insertion tool has first and second projections extending from the distal end and positioned to engage the first and second sidewalls of the intervertebral cage, wherein the insertion tool defines first and second tool anchor guides at the distal end, and wherein the distal end of the insertion tool is configured to engage the intervertebral cage with the first and second tool anchor guides aligned with the first and second internal anchor guides of the intervertebral cage.

17. A method of operating the implant system of claim 16, the method comprising:

preparing a disc space in a lateral aspect of a lumbar spine to receive the intervertebral cage;

inserting the intervertebral cage posteriorly into the lateral aspect of the disc space of the lumbar spine;

after the intervertebral cage is positioned in the lateral aspect of the disc space, inserting the first anchor posteriorly through the first internal anchor guide and into the first vertebral body to secure the intervertebral cage with respect to the first vertebral body; and after the intervertebral cage is positioned in the lateral aspect of the disc space, inserting the second anchor posteriorly through the second internal anchor guide and into the second vertebral body to secure the intervertebral cage with respect to the second vertebral body.

18. The method of claim 17, wherein the intervertebral cage is inserted via the insertion tool and wherein the first and second anchors are inserted through the first and second tool anchor guides, respectively, into the first and second internal anchor guides, respectively, while the insertion tool is engaged with the intervertebral cage.

19. The implant system of claim 16, wherein the bottom surface of the bottom wall intersects with the first and second disc-facing surfaces at first and second curved corners and wherein the top surface of the top wall intersects with the first and second disc-facing surfaces at first and second perpendicular corners.

20. The implant system of claim 16, wherein the first and second anchors comprise self-tapping screws having a threaded body.

* * * * *